United States Patent
Rini et al.

(10) Patent No.: US 7,479,108 B2
(45) Date of Patent: Jan. 20, 2009

(54) METHODS FOR USING AN IMPLANTABLE SENSOR UNIT

(75) Inventors: Christopher J. Rini, Raleigh, NC (US); Robert D. Black, Chapel Hill, NC (US)

(73) Assignee: Sicel Technologies, Inc., Morrisville, NC (US)

( * ) Notice: Subject to any disclaimer, the term of this patent is extended or adjusted under 35 U.S.C. 154(b) by 24 days.

(21) Appl. No.: 11/403,522

(22) Filed: Apr. 13, 2006

(65) Prior Publication Data

US 2006/0183979 A1 Aug. 17, 2006

Related U.S. Application Data

(62) Division of application No. 10/353,857, filed on Jan. 28, 2003, now abandoned.

(60) Provisional application No. 60/352,912, filed on Jan. 29, 2002.

(51) Int. Cl.
*A61B 5/00* (2006.01)
(52) U.S. Cl. .................... 600/300; 600/426
(58) Field of Classification Search ................. 600/300, 600/301, 426; 128/903–905, 920
See application file for complete search history.

(56) References Cited

U.S. PATENT DOCUMENTS

| | | | |
|---|---|---|---|
| 4,142,383 A | 3/1979 | Eberhart | |
| 4,361,153 A | 11/1982 | Slocum et al. | |
| 4,494,545 A | 1/1985 | Slocum et al. | |
| 4,519,401 A | 5/1985 | Ko et al. | |
| 4,703,756 A | 11/1987 | Gough et al. | |
| 4,796,641 A | 1/1989 | Mills et al. | |
| 4,846,191 A | 7/1989 | Brockway et al. | |
| 4,976,266 A | 12/1990 | Huffman et al. | |
| 5,011,494 A | * 4/1991 | von Recum et al. | 623/23.74 |
| 5,074,318 A | 12/1991 | Campbell et al. | |
| 5,121,748 A | 6/1992 | Ditz et al. | |
| 5,148,404 A | 9/1992 | Hilferink et al. | |
| 5,166,073 A | 11/1992 | Lefkowitz et al. | 436/57 |

(Continued)

FOREIGN PATENT DOCUMENTS

EP 0 245 073 B1 11/1987

(Continued)

OTHER PUBLICATIONS

Akin, T., Z. Babak, K. Najafi, "RF telemetry powering and control of hermetically sealed integrated sensors and actuators," Proc. Solid-State Sensors & Actuators Workshop, Hilton Head, SC, 1990, pp. 145-148.

(Continued)

*Primary Examiner*—Michael C Astorino
*Assistant Examiner*—Kai Rajan
(74) *Attorney, Agent, or Firm*—Myers Bigel Sibley & Sajovec, PA

(57) ABSTRACT

A method for obtaining data using an implantable sensor unit in a body of a patient includes: implanting the sensor unit in the body; conducting an imaging procedure on the body such that the sensor unit in the body serves as a fiducial marker; detecting a parameter using the sensor unit in the body; and transmitting data associated with the detected parameter from the sensor unit to a remote receiver unit.

35 Claims, 15 Drawing Sheets

U.S. PATENT DOCUMENTS

| | | | | |
|---|---|---|---|---|
| 5,178,164 | A | * | 1/1993 | Allen .................... 128/898 |
| 5,314,458 | A | * | 5/1994 | Najafi et al. ............. 607/116 |
| 5,372,133 | A | | 12/1994 | Hogen Esch |
| 5,535,752 | A | | 7/1996 | Halperin et al. |
| 5,557,702 | A | | 9/1996 | Yoshikawa et al. .......... 385/143 |
| 5,564,434 | A | | 10/1996 | Halperin et al. |
| 5,640,764 | A | * | 6/1997 | Strojnik ................... 29/856 |
| 5,681,611 | A | | 10/1997 | Yoshikawa et al. ....... 427/163.2 |
| 5,731,957 | A | | 3/1998 | Brennan |
| 5,811,814 | A | | 9/1998 | Leone et al. ............. 250/368 |
| 5,833,603 | A | | 11/1998 | Kovacs et al. |
| 5,840,148 | A | | 11/1998 | Campbell et al. |
| 5,916,167 | A | | 6/1999 | Kramer et al. ............ 600/436 |
| 5,963,132 | A | | 10/1999 | Yaokum |
| 6,001,067 | A | | 12/1999 | Shults et al. .............. 600/584 |
| 6,015,390 | A | | 1/2000 | Krag ..................... 600/549 |
| 6,239,724 | B1 | | 5/2001 | Doron et al. .......... 340/870.28 |
| 6,240,312 | B1 | | 5/2001 | Alfano et al. |
| 6,242,741 | B1 | | 6/2001 | Miller et al. .......... 250/363.02 |
| 6,295,680 | B1 | | 10/2001 | Wahl et al. ................... 14/1 |
| 6,304,766 | B1 | * | 10/2001 | Colvin, Jr. .............. 600/317 |
| 6,330,464 | B1 | * | 12/2001 | Colvin et al. ............ 600/316 |
| 6,363,940 | B1 | | 4/2002 | Krag ..................... 128/899 |
| 6,402,689 | B1 | * | 6/2002 | Scarantino et al. .......... 600/300 |
| 6,444,475 | B1 | | 9/2002 | Anderson, Jr. et al. ...... 436/161 |
| 6,491,639 | B1 | * | 12/2002 | Turcott ................... 600/508 |
| 6,689,056 | B1 | * | 2/2004 | Kilcoyne et al. ............ 600/300 |
| 6,749,553 | B2 | * | 6/2004 | Brauckman et al. ............ 600/3 |

FOREIGN PATENT DOCUMENTS

| | | |
|---|---|---|
| EP | 0 364 045 A1 | 4/1990 |
| EP | 0 364 045 B1 | 4/1990 |
| EP | 0 537 761 A2 | 4/1993 |
| WO | WO 95/17809 A1 | 7/1995 |
| WO | WO 97/33513 A1 | 9/1997 |
| WO | WO 98/02209 A2 | 1/1998 |
| WO | WO 98/43701 A1 | 10/1998 |
| WO | WO 00/18294 | 4/2000 |
| WO | WO 01/22874 A1 | 4/2001 |
| WO | WO 02/39917 | 5/2002 |
| WO | WO 02/39918 | 5/2002 |
| WO | WO 02/100485 A1 | 12/2002 |

OTHER PUBLICATIONS

Brochure, "Be as smart as you can be with BMDS and Smart Alec™ your partners in intelligence," Bio Medic Data Systems, Inc. (© 1999).

Brochure, "Come along for the incredible journey in the development of the IPTT-200," Bio Medic Data Systems, Inc. (© 2000).

Gilligan et al., "Evaluation of a subcutaneous glucose sensor out to 3 months in a dog model," *Diabetes Care,* vol. 17, pp. 882-887 (1994).

Loeb et al., "Injectable microstimulator for functional electrical stimulation," *Med. & Biol. Eng. & Comput.,* vol. 29. pp. NS13-NS19 (1991).

Nardin et al., "A multichannel neuromuscular microstimulator with bidirectional telemetry," Proc. Int. Conf. on Solid-State Sensors and Actuators, Stockholm, Sweden, vol. 1, pp. 59-62 (Jun. 1995).

Oshima et al., "Development of micro-telemetering, multi-sensor capsule system with newly developed LSI for clinical applications," Proc. Int. Conf. on Solid-State Sensors and Actuators, pp. 163-166 (1987).

Pregelj et al., "Leak detection methods and defining the sizes of leaks", NDT.net, vol. 4, No. 2, 8 pp. (Feb. 1999).

International Search Report for PCT/US03/02570 dated Jun. 10, 2003.

\* cited by examiner

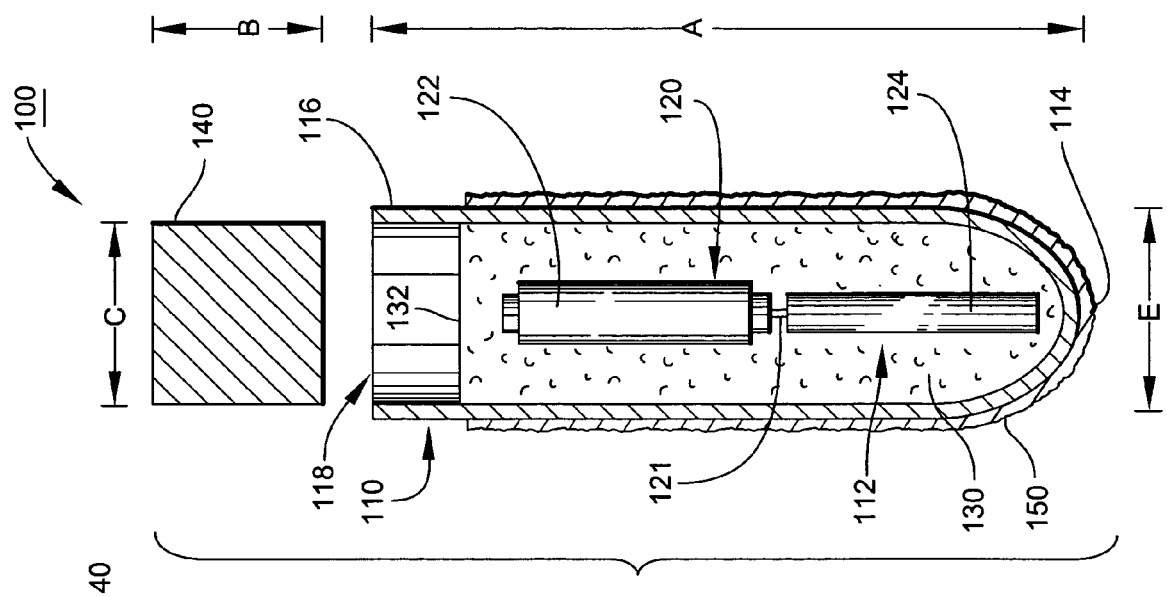
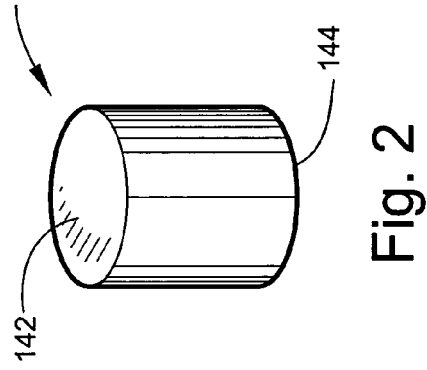
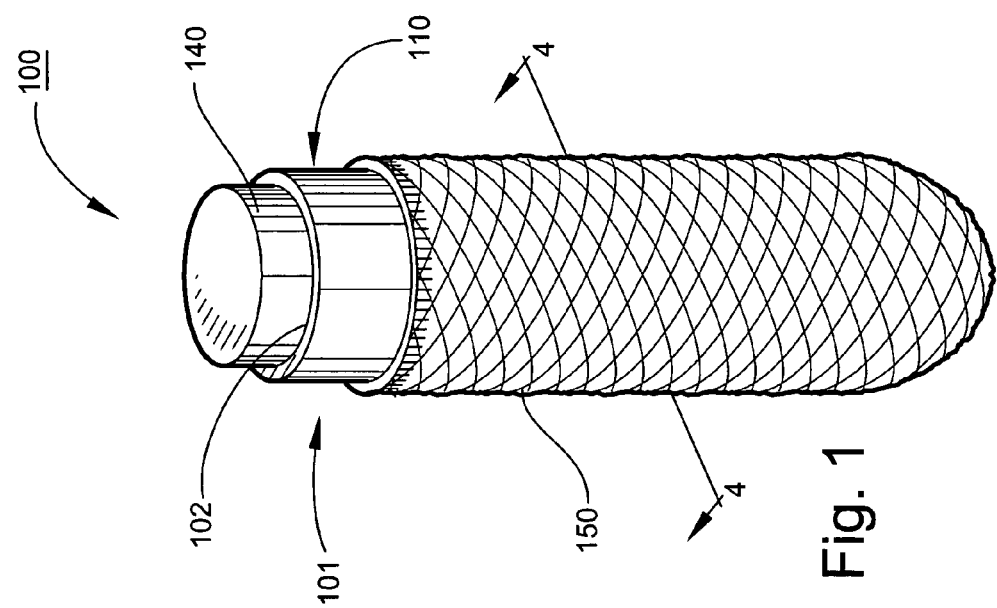

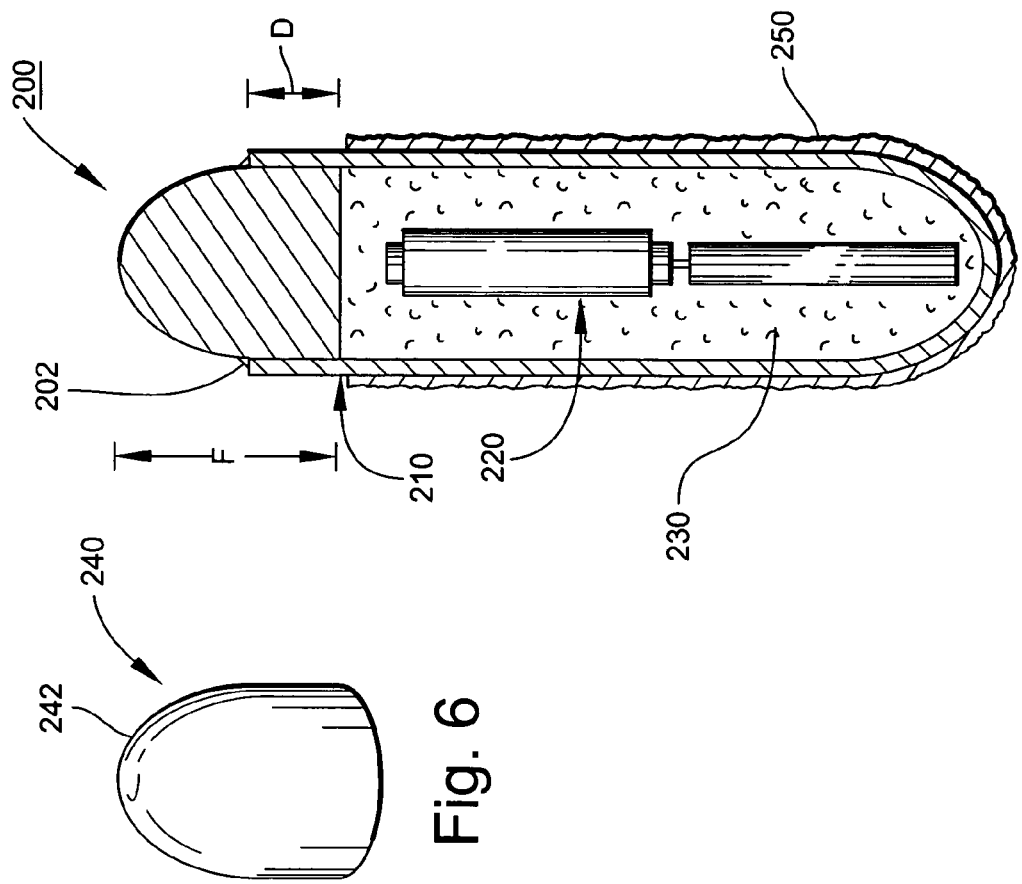
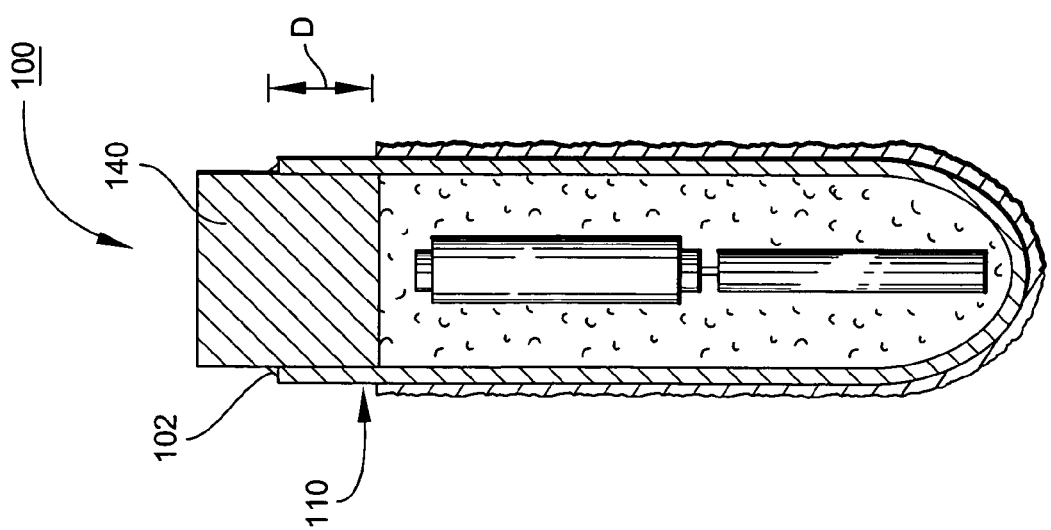

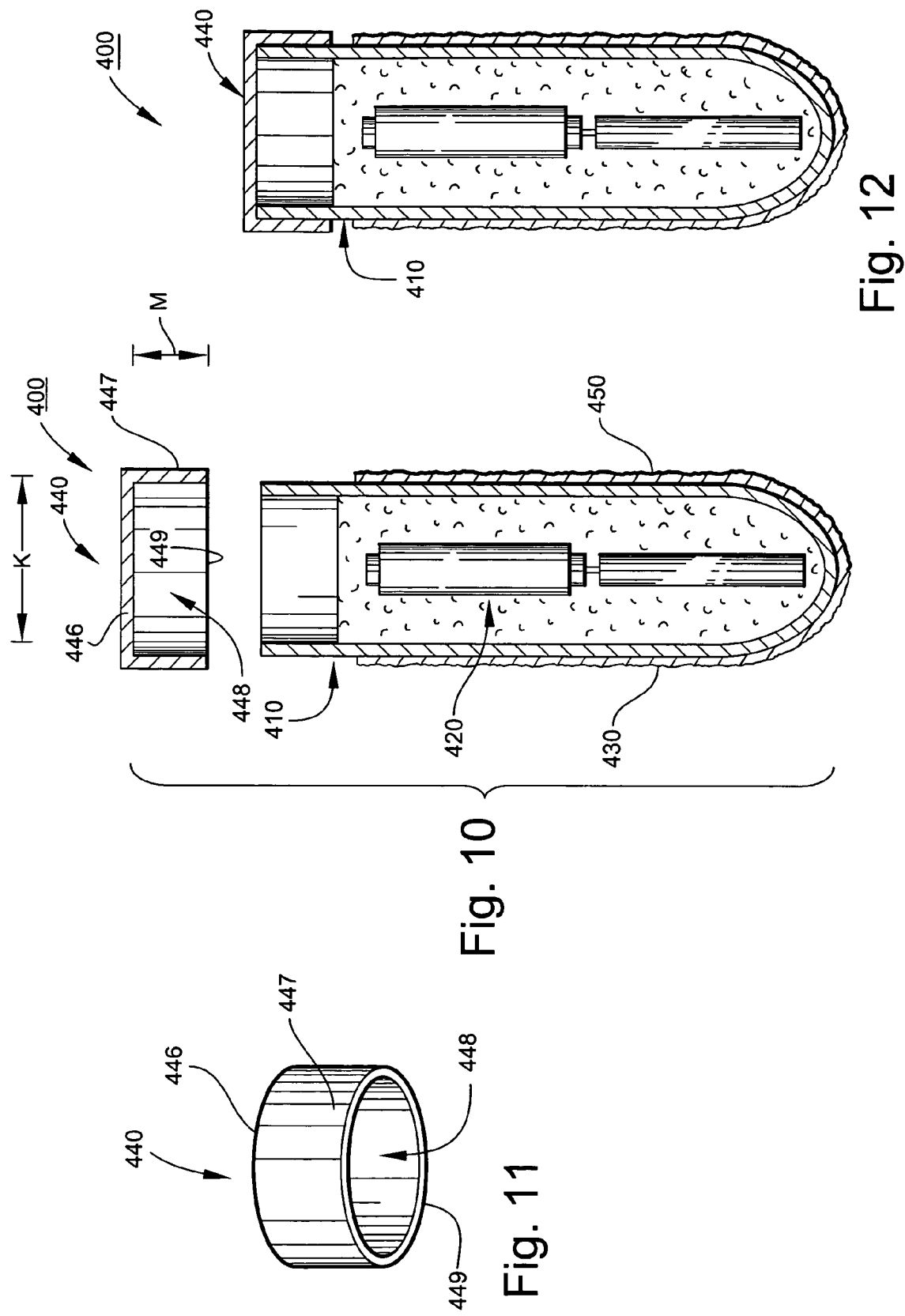

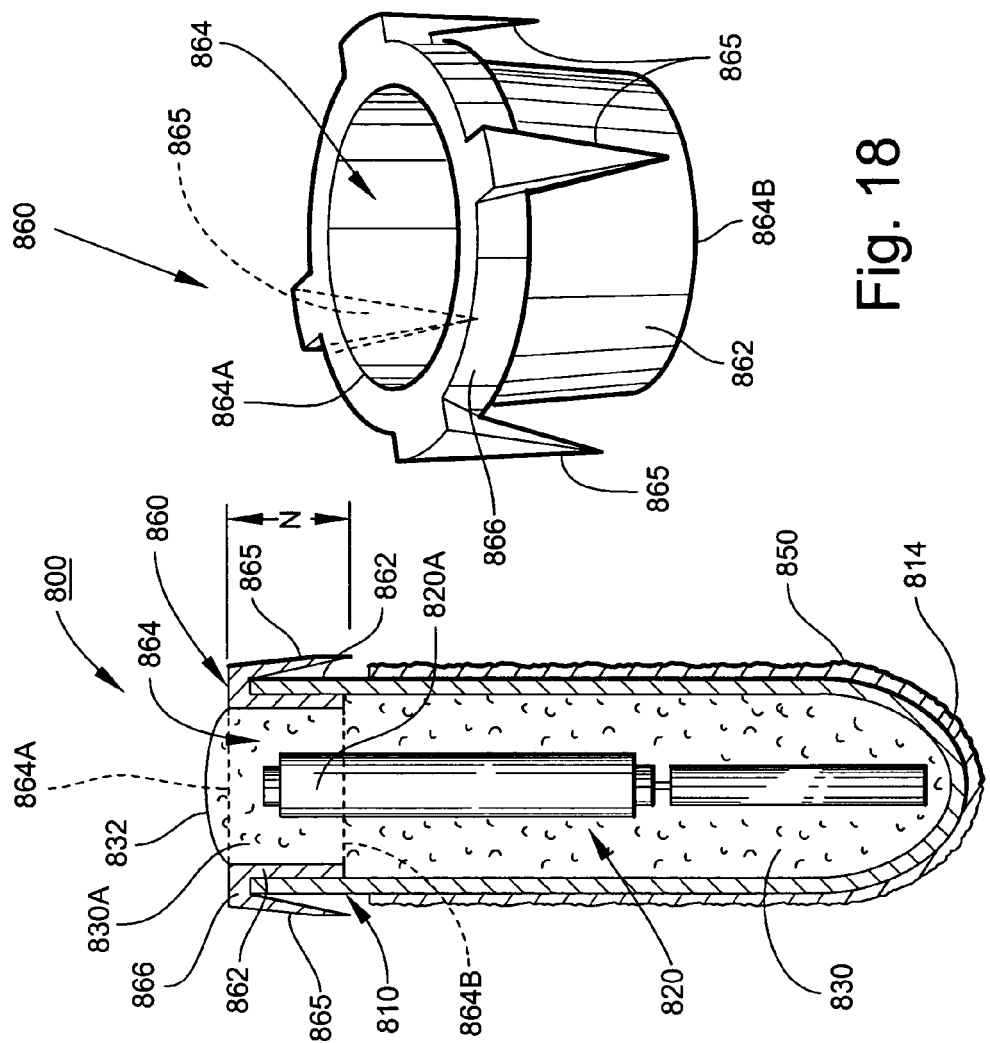
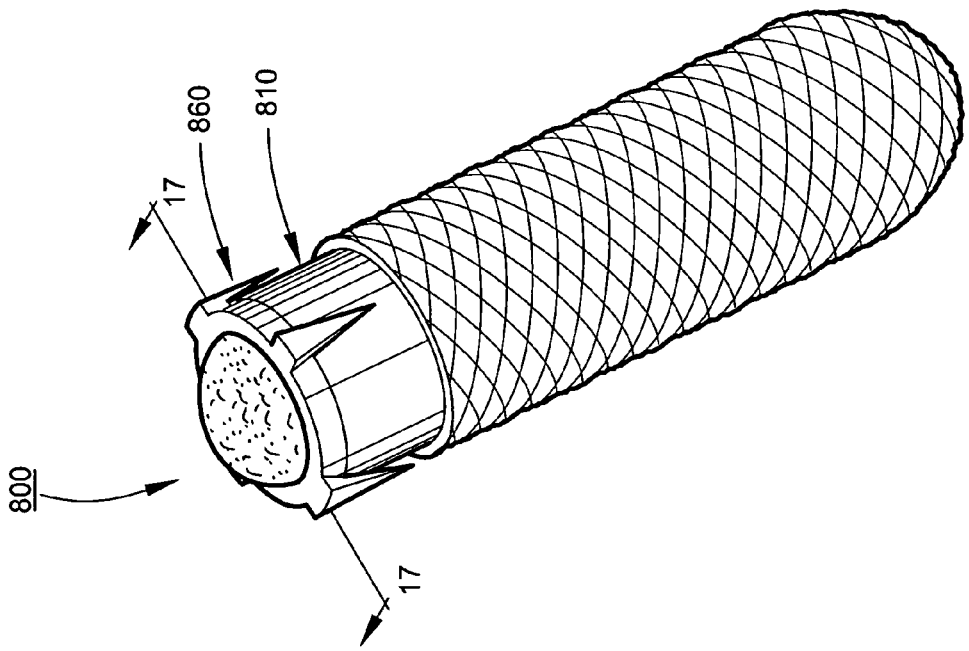

METHODS FOR USING AN IMPLANTABLE SENSOR UNIT

RELATED APPLICATIONS

The present application is a divisional application of U.S. patent application Ser. No. 10/353,857, filed Jan. 28, 2003, now abandoned, which claims the benefit of and priority from U.S. Provisional Application Ser. No. 60/352,912, filed Jan. 29, 2002, the disclosures of which are hereby incorporated herein by reference in their entireties.

FIELD OF THE INVENTION

The present invention relates to sensors and, more particularly, to a sensor housing or a sensor unit which may be implanted in the body of a human or other animal, and methods for forming and using the same.

BACKGROUND OF THE INVENTION

Sensors or markers may be implanted into the body of a human or other animal patient to facilitate diagnosis, treatment or identification. The sensor or marker may include various electronics and a surrounding housing. For example, a sensor may include electronics as needed to detect or measure parameters of the surrounding environment. The sensor or marker may also include electronics for wireless communication with a receiver unit located outside of the patient's body.

It is often desirable to maintain the sensor or marker as described above in a particular location or region in the patient. Migration of the sensor or marker may diminish the effectiveness of the sensor or marker to accurately sense the desired parameters.

The surrounding environment of the implanted sensor or marker can include physiological fluid, cells and tissue. The surrounding fluids or moisture from the surrounding cells and/or tissue may hydrate the sensor, and this intruding moisture may promote corrosion of or otherwise damage or interfere with the operation of the aforementioned electronics.

SUMMARY OF THE INVENTION

According to embodiments of the present invention, an in vivo implantable sensor unit includes a glass sensor housing defining an elongated chamber. Sensor electronics are disposed in the chamber. The sensor electronics are adapted to wirelessly transmit data. The sensor unit is configured to wirelessly transmit data from an in vivo position to a remote receiver over a period of at least four weeks and the sensor housing is adapted to provide a hermetic seal about the sensor electronics for a period of at least four weeks. The hermetic seal is such that under a helium mass spectrometer leak detection test the sensor housing has a leak rate that is less than about $10^{-8}$ atm-cc/s.

According to further embodiments of the present invention, an implantable sensor unit includes a tube defining a chamber and an opening communicating with the chamber. Sensor electronics are disposed in the chamber. Epoxy is disposed in the chamber and surrounds the sensor electronics. The epoxy has an end surface adjacent the opening of the tube. An end plug is mounted in the opening of the tube. The end surface of the epoxy and the end plug define a gap therebetween configured to insulate the sensor electronics.

According to still further embodiments of the present invention, an implantable sensor unit includes a tube defining an elongated chamber and an opening communicating with the chamber. Sensor electronics are disposed in the chamber. An end plug is mounted in the opening of the tube. The end plug is spherically shaped.

According to further embodiments of the present invention, an implantable sensor unit includes a tube defining a chamber and an opening communicating with the chamber. Sensor electronics are disposed in the chamber. Epoxy is disposed in the chamber and surrounds the sensor electronics. The epoxy has an end surface adjacent the opening of the tube. The sensor unit further includes a retaining cap including at least one projection extending outwardly from the tube. The retaining cap is secured to the tube by the epoxy.

According to embodiments of the present invention, an implantable sensor unit includes a sensor housing defining an elongated chamber. Sensor electronics are disposed in the chamber. A retention device is mounted on the sensor housing. The retention device includes a band surrounding a portion of the sensor housing and at least one projection secured to and extending from the band.

According to further embodiments of the present invention, an implantable sensor unit includes a sensor housing having an outer surface and defining a chamber. Sensor electronics are disposed in the chamber. The sensor electronics are adapted to wirelessly transmit data. A bio-compatible anti-migration coating is disposed on the outer surface. The anti-migration coating is a Parylene C coating.

According to still further embodiments of the present invention, an implantable sensor unit includes a sensor housing having an outer surface and defining a chamber. A bio-compatible anti-migration mesh layer is disposed on the outer surface.

According to method embodiments of the present invention, a method for forming a sensor unit includes: inserting an uncured epoxy into a tube in a fluid state; inserting sensor electronics into the uncured epoxy in the tube; evacuating air bubbles from the epoxy and the sensor electronics in the tube; and then curing the epoxy.

According to further method embodiments of the present invention, a method for forming a sensor unit includes: inserting an uncured epoxy in a fluid state into a tube through an opening in the tube; inserting sensor electronics into the uncured epoxy; curing the epoxy such that the epoxy stabilizes the sensor electronics; and sealing the opening in the tube to form a hermetically sealed tube.

According to further method embodiments of the present invention, a method for forming a sensor unit includes: providing a sensor housing having an outer surface and defining a chamber; providing sensor electronics in the chamber, wherein the sensor electronics are adapted to wirelessly transmit data; and applying a bio-compatible anti-migration coating to the outer surface of the sensor housing using a plasma polymerization thin film deposition technique.

According to further method embodiments of the present invention, a method for forming a sensor unit includes: providing a sensor housing having an outer surface and defining a chamber; providing sensor electronics in the chamber, wherein the sensor electronics are adapted to wirelessly transmit data; and applying a bio-compatible anti-migration coating to the outer surface of the sensor housing, wherein the anti-migration coating is a Parylene C coating.

According to further method embodiments of the present invention, a method for forming a sensor unit includes: applying a bio-compatible anti-migration mesh layer to an outer surface of a sensor housing.

According to further method embodiments of the present invention, an implantable sensor unit includes a sensor housing having an outer surface. A bio-compatible anti-migration layer surrounds at least a portion of the outer surface of the sensor housing. The anti-migration layer is formed of a textile material.

According to further method embodiments of the present invention, a method for forming an implantable sensor unit includes: providing a sensor housing; and placing a bio-compatible anti-migration layer over the outer surface of the sensor housing, the anti-migration layer being formed of a textile material.

According to further embodiments of the present invention, an implantable sensor unit includes a sensor housing having an end and defining a chamber. Sensor electronics are disposed in the chamber. A holding tab extends from the end of the housing. The holding tab is adapted to facilitate handling of the housing.

According to further method embodiments of the present invention, a method for implanting an implantable sensor unit in a body, the sensor unit including a sensor housing, includes handling the sensor housing in the body using a holding tab extending from an end of the housing.

According to further method embodiments of the present invention, a method for using an implantable sensor unit in a body includes: implanting the sensor unit in the body; conducting an imaging procedure on the body such that the sensor unit in the body serves as a fiducial marker; detecting a parameter using the sensor unit in the body; and transmitting data associated with the detected parameter from the sensor unit to a remote receiver unit.

According to still further embodiments of the present invention, an implantable sensor unit includes a sensor housing having an outer surface. A bio-compatible anti-migration layer surrounds at least a portion of the outer surface of the sensor housing. The anti-migration layer is formed of a heat shrinkable thermoplastic material.

According to further method embodiments of the present invention, a method for forming a sensor unit includes: providing a sensor housing having an outer surface and defining a chamber; providing sensor electronics in the chamber, wherein the sensor electronics are adapted to wireless transmit data; placing a bio-compatible anti-migration layer about the sensor housing, wherein the anti-migration layer is formed of a heat shrinkable thermoplastic material; and heating the anti-migration layer to shrink the anti-migration layer about the sensor housing.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 1 is a perspective view of a sensor unit according to embodiments of the present invention;

FIG. 2 is a perspective view of a plug forming a part of the sensor unit of FIG. 1 according to embodiments of the present invention;

FIG. 3 is an exploded, cross-sectional view of the sensor unit of FIG. 1 taken along the line 4-4 of FIG. 1;

FIG. 4 is a cross-sectional view of the assembled sensor unit of FIG. 1 taken along the line 4-4 of FIG. 1;

FIG. 5 is a cross-sectional view of a sensor unit according to further embodiments of the present invention;

FIG. 6 is a perspective view of a plug forming a part of the sensor unit of FIG. 5;

FIG. 10 is an exploded, cross-sectional view of a sensor unit according to further embodiments of the present invention;

FIG. 11 is a perspective view of a cap forming a part of the sensor unit of FIG. 10;

FIG. 12 is a cross-sectional view of the assembled sensor unit of FIG. 10;

FIG. 16 is a perspective view of a sensor unit according to yet further embodiments of the present invention;

FIG. 17 is a cross-sectional view of the sensor unit of FIG. 16 taken along the line 17-17 of FIG. 16;

FIG. 18 is a perspective view of a retention cap forming a part of the sensor unit of FIG. 16;

DETAILED DESCRIPTION OF EMBODIMENTS OF THE INVENTION

Figure 9:
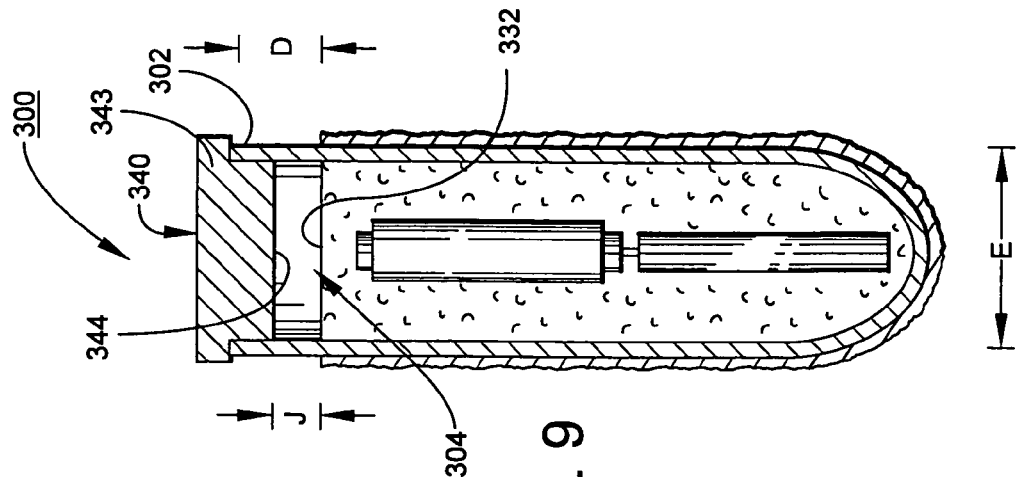
FIG. 9 is a cross-sectional view of the assembled sensor unit of FIG. 7.

The present invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, layers, components or regions may be exaggerated for clarity.

As used herein, "textile material" means an article having structural integrity resulting from forced interassociation of a plurality of fibers, filaments, or strands, the forced interassociation resulting from processes such as weaving, knitting, braiding, needling hydroentangling, chemical coating or impregnation, autogenous bonding (i.e., heat- and/or pressure-promoted welding or solvent bonding) or felting.

As used herein, "multi-filament textile material" means a textile material having structural integrity resulting from forced interassociation of a plurality of filaments.

As used herein, "braided material" means a textile material in which one or more yarns, filaments or strands pass alternately over or under one or more other strands; or in which one or more strands half-twist alternately about two or more adjacent strands.

A desired function for an implantable sensor may be to sense a physical parameter and transmit this information for analysis. However, these parameters may only be interpreted with meaning if the sensor is in a specific location in the body. With this limitation, a design parameter for the device may be to keep the sensor in a desired location so that it is retained at the target implant site. The present invention may satisfy certain design parameters not only to ensure the safety of such a device, but also to produce reliable data from a specific implant location for a prolonged time period. The present invention may meet the more stringent regulations imposed on devices for use in humans. The present invention may also insure compatibility of tissue/blood contacting materials as well as device function compliance and approval. Embodiments of the invention include materials selection for biocompatibility and function, moisture resistant design of components used for hermetic sealing, as well as novel means for retaining the implant in a desired location.

In certain embodiments, the sensor units of the present invention may be implanted (e.g., injected) into various tissues of any animal subject, preferably mammalian subjects (e.g., humans, canines, felines, bovines, caprines, ovines, equines, rodents, porcines, and/or lagomorphs), and more preferably human subjects. The sensor units may be cost-effectively manufactured and implanted in or otherwise positioned at desired locations in or proximate to tissues or organs in the body and may be particularly suitable to position adjacent or in cancerous tumors.

The sensor units described herein are particularly well-suited for use in monitoring systems, methods, and associated devices as disclosed in U.S. Pat. No. 6,402,689 issued Jun. 11, 2002, the disclosure of which is hereby incorporated herein by reference in its entirety. As described, the sensor unit can dynamically monitor multiple tumor physiological and biological parameters and/or changes associated with tumors to identify enhanced or favorable treatment conditions to thereby establish a patient-specific treatment delivery time or patient-specific treatment. The methods disclosed in U.S. Pat. No. 6,402,689 include methods of monitoring at least one physiological parameter associated with a tumor in a subject undergoing medical treatment with an in vivo sensor. Data associated with at least one monitored physiological parameter is wirelessly transmitted from an in vivo sensor to a receiver external of the subject. The transmitted data is analyzed and processed into meaningful parameters that may indicate how the tumor is responding to treatment. Additional data is transmitted and analyzed periodically at a plurality of sequential points in time, and a tumor treatment strategy is evaluated based on the analyzing step. The sensor units of the present invention can be used to monitor, in substantially real time and/or dynamically, specific indices associated with tumor physiology making monitored data available for immediate use in treatment decisions. Thus, the sensor units may be used to provide sufficient ongoing, and preferably substantially real-time, information pertaining to the physiological and/or biological condition of the tumor during a treatment period in a manner that provides the information to the physician to allow the physician to make informed therapeutic decisions.

Moreover, the sensor units of the present invention may be used in the in vivo evaluation and monitoring of tumors prior to, during, and subsequent to an active treatment, and preferably over an entire treatment regime or period. That is, the sensor units are particularly suitable for monitoring the behavior of cancerous tumors such as sarcomas and carcinomas over a particular non-remission treatment period. As such, the sensor units of the present invention are preferably configured to be biocompatible and provide at minimum a service life suitable for episodic treatment evaluation of at least about 4-6 weeks, and more preferably at least about 6-10 weeks, and still more preferably at least about 10-12 weeks, whether exposed to radiation, chemotherapy, heat or ionic electric fields (such as the treatment provided by a Thermotron® machine) directed to the tumor.

With reference to FIGS. 1-4, a sensor unit according to embodiments of the present invention is shown therein and generally designated by the number 100. The sensor unit 100 includes generally a sensor housing 101 (FIG. 1), and sensor electronics 120 and epoxy 130 disposed within the sensor housing 101. The sensor housing 101 includes a tube 110, a plug 140 and an optional anti-migration coating 150 disposed over a portion or all of the outer surface of the sensor unit 100.

In certain embodiments, the tube 110 is cylindrically shaped and sized for injection through a trocar/cannula assembly, syringe or catheter, for example, into human tissue. The tube 110 defines an interior chamber 112. The tube 110 has a tapered or rounded, closed end 114 (FIG. 3) to facilitate easier entry into the target tissue (e.g., the tumor). As shown in FIG. 3, the tube 110 further has an open end 116 opposite the closed end 114. The rim at the open end 116 is preferably smooth and defines an opening 118 which, in the absence of the plug 140, fluidly communicates with the chamber 112. Preferably, the length A (FIG. 1) of the tube 110 is between about 10 and 27 mm. In certain embodiments, the inner diameter E (FIG. 3) of the tube 110 can be between about 1.5 and 2.5 mm. While the wall thickness of the tube 110 can be between about 0.15 and 0.56 mm. Similarly, the chamber 112 can have a volume of between about 16 and 127 mm$^3$.

The tube 110 can be formed of a bio-compatible material. In certain embodiments, the tube 110 is formed of a bio-compatible silicate, preferably a bio-compatible glass. Suitable bio-compatible glasses include, for example, glass as described in U.S. Pat. No. 5,121,748 to Ditz et al. (assigned to Schott Glaswerke of Germany). Preferably, the entire sensor unit 100 is sterilized using a means that does not adversely affect the sensor's electronic components or housing materials before being injected or implanted.

The sensor electronics 120 are disposed in the chamber 112. The sensor electronics 120 may include suitable components to measure temperature, level of oxygenation, cell proliferation, tumor or normal tissue pH, externally generated radiation and/or radiolabeled substances. The sensor unit 100 may include components suitable to provide a telemetry link to wirelessly communicate with an remotely or externally located receiver. The sensor electronics 120 may include various electronics such as those described in U.S. Pat. No. 6,402,689 and in PCT International Application No. PCT/USOO/08310, filed Mar. 9, 2000, the disclosures of which are hereby incorporated herein in their entireties by reference. Accordingly, the electronic components 120 described herein are exemplary and are not exhaustive of the components which may be housed in the sensor unit 100. As illustrated, the sensor electronics 120 include a printed circuit board (PCB) or integrated circuit (IC) chip 124 including circuitry operative to measure and process the desired environmental and physical parameter(s) (e.g., pH, gamma radiation, and fluorescence). The circuitry may include a power source such as a battery. An antenna portion 122 is positioned above the IC 124. The antenna portion 122 may be formed to include a cylindrically wrapped antenna coil. Other antenna configurations can also be used as is known to those of skill in the art. The antenna portion 122 is joined to the IC 124 at a juncture 121.

As shown in FIG. 3, the sensor electronics 120 can be substantially entirely surrounded by the epoxy 130, which is cured to a non-flowable or solid state. Preferably, the epoxy 130 fills a predominant portion, but less than all of the chamber 112. More preferably, as shown in FIG. 4, the upper surface 132 of the cured epoxy is disposed below the end 116 a length D of between about 2 and 8 mm. The volume of epoxy 130 may surround all or portions of the circuit board 124 and/or the antenna portion 122. Preferably, the epoxy 130 surrounds or encapsulates at least a portion of the antenna portion 122 and all of the juncture 121 in order to stabilize and secure the electronic portions 122 and 124 to one another. The volume may be dependent on the method of sealing the housing.

The epoxy 130 can be USP Class VI epoxy material. Suitable epoxy materials include Product No. EPO-PEK301-2 available from Epoxy Technology Incorporated of Billerica, Mass.

As shown in FIG. 2, the plug 140 is substantially solid and cylindrical, and has blunt (e.g., flat) opposed end surfaces 142 and 144. Preferably, the plug 140 is formed of the same glass material as the tube 110. The length B (FIG. 3) of the plug can be between about 4 and 8 mm. The diameter C (FIG. 3) of the plug 140 is preferably substantially the same as the inner diameter E of the tube 110.

The anti-migration coating 150 is disposed on an exterior surface of the tube 110. The anti-migration coating 150 is a selected coating adapted to inhibit significant migration of the sensor unit 100 when the sensor unit 100 is positioned in the targeted tissue. Preferably, the coating 150 is bio-compatible, and more preferably a Class VI medical grade coating. Preferably, the coating 150 promotes attachment of live tissue to the coated tube 110. The anti-migration coating 150 may be a polymer coating, preferably a Parylene C conformal coating, an epoxy coating or a polypropylene coating. In certain embodiments, the anti-migration coating 150 has a higher coefficient of friction in an in vivo environment than the underlying tube 110. The coating 150 may be hydrophobic. If desired, the anti-migration coating 150 may be omitted from the sensor unit 100 and from each of the sensor unit embodiments described below. The anti-migration coating 150 may cover all or a portion less than all of the outer surface of the tube 110.

The sensor unit 100 may be assembled in the following manner. A volume of uncured epoxy 130 material is injected into the chamber 112. The sensor electronics 120 are inserted into the uncured epoxy 130. The electronics 120 may settle to or adjacent the lower end of the tube 110. The tube 110, the epoxy 130 and the electronics 120 are subjected to a vacuum atmosphere to draw trapped air (e.g., air potentially trapped in the coil 122) out of the epoxy. The epoxy may be subjected to a vacuum of between about 5 and 30 inches of mercury (in Hg) for a time of between about 15 and 60 minutes. The epoxy 130 is then cured by time, chemical process, and/or exposure to heat or light. The plug 140 is then inserted into the opening 118 of the tube 110 as shown in FIG. 3 until the end face 144 abuts the upper surface 132 of the cured epoxy 130. The plug 140 and the tube 110 are then circumferentially laser welded (e.g., using an infrared laser) or flamed together to form a weld seal 102, preferably at a distance away from the epoxy 130 and the sensor electronics 120. Other coupling or sealing means can also be used, such as brazing, adhesives, fusing the glass, O-rings and threaded attachment means. The weld seal 102 so formed may be a hermetic seal. The anti-migration coating 150 is applied to the outer surface of the tube 110. Alternatively, the anti-migration coating may be applied to all or portions of the tube 110 before the epoxy is injected into the tube 110. The entire sensor unit 100 may then be sterilized.

The anti-migration coating 150 may be applied to the outer surface of the tube 150 using a plasma polymerization thin film deposition or a vapor deposition polymerization (VDP) technique. For example, the coating may be a Parylene C coating applied by VDP and preferably having a thickness of between about 10,000 and 60,000 Angstroms. Alternatively, the coating 150 may be a plasma polymerized thin film coating (preferably a plasma polypropylene thin film) having a thickness of between about 4,000 and 60,000 Angstroms. Suitable plasma deposition techniques and equipment may be provided by Plasmatech, Inc. of Erlanger, Ky. Suitable VDP techniques and equipment may be provided by Specialty Coating Systems of Clear Lake, Wis.

With reference to FIGS. 5 and 6, a sensor unit 200 according to further embodiments of the present invention is shown therein. The sensor unit 200 includes elements 210, 220, 230 and 250 corresponding to elements 110, 120, 130 and 150, respectively, of the sensor unit 100. The sensor unit 200 differs from the sensor unit 100 in that the plug 140 is replaced with a plug 240 having a rounded or dome-shaped outer end 242. Preferably, the plug 240 has a length F (FIG. 5) of between about 4 and 8 mm. The plug 240 otherwise corresponds to the plug 140. The sensor unit 200 may be formed in the same manner as described above with regard to the sensor unit 100.

Figure 7:
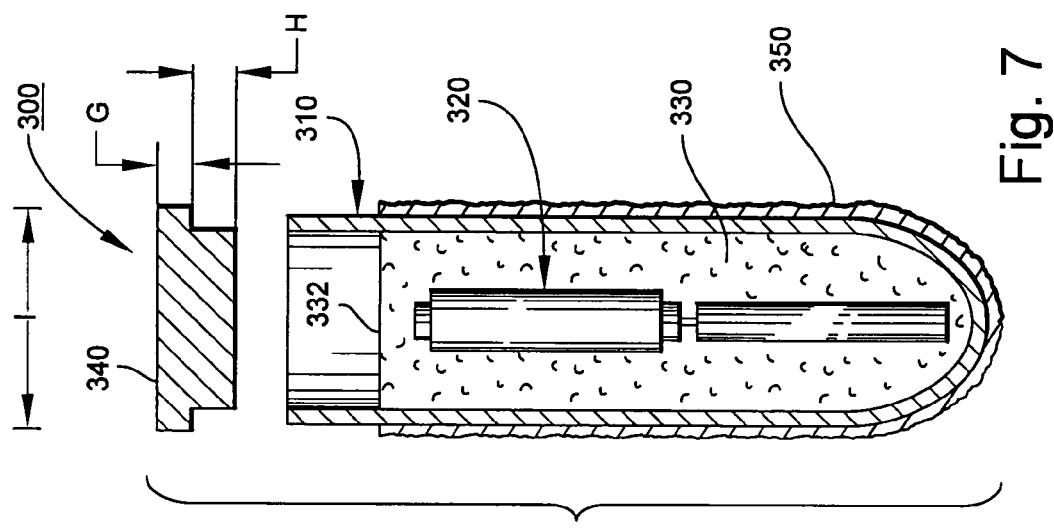
FIG. 7 is an exploded, cross-sectional view of a sensor unit according to further embodiments of the present invention.
Figure 8:
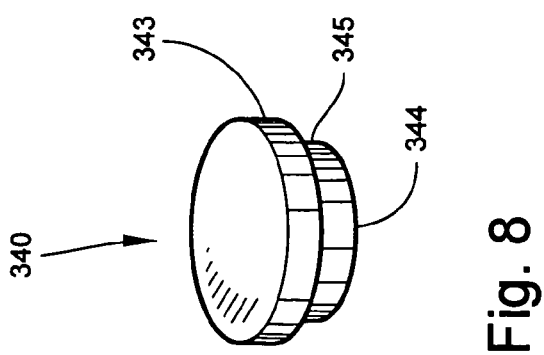
FIG. 8 is a perspective view of a plug forming a part of the sensor unit of FIG. 7.

With reference to FIGS. 7-9, a sensor unit 300 according to further embodiments of the present invention is shown therein. The sensor unit 300 has elements 310, 320, 330 and 350 corresponding to the elements 110, 120, 130 and 150, respectively, of the sensor unit 100. The sensor unit 300 has a plug 340 in place of the plug 140.

The plug 340 may be formed of the same materials as discussed above with regard to the plug 140. As illustrated, the plug 340 is formed as a solid member; however, the cap 340 may be hollow with a closed outer surface. The plug 340 has an enlarged outer portion 343 having a diameter I (FIG. 7) that is greater than the inner diameter E (FIG. 9) of the tube 310 and, preferably, equal to or greater than the outside diameter of the tube 310. The plug 340 also has an inner portion 345 having the same relative diameter as the plug 140 (i.e., substantially the same as the inner diameter E). In this way the bottom portion 345 of the plug is received into the tube 310. Preferably, the upper plug outer portion 343 has a length G (FIG. 7) of between about 1 and 5 mm. A seal 302 (FIG. 9) is formed between the rim of the tube 310 and the plug portion 343.

As shown in FIG. 9, the length H (FIG. 7) of the inner portion 345 is selected relative to the depth D (FIG. 9) of the upper surface 332 of the epoxy 330 such that a gap 304 is defined between the inner surface 344 of the plug 340 and the end surface 332 of the epoxy 330. Preferably, the length H is selected relative to the depth D such that the gap 304 has a length J (FIG. 9) of between about 2 and 10 mm. The gap 304 may be filled with air or other suitable fluid or suitable solid material that may serve to insulate the electronics from heat. The gap 304 may serve to insulate the electronics 320 from heat, for example, during the laser welding or flaming procedure used to form the weld seal 302. Preferably, the volume and height of the gap 304 are sufficient to prevent the epoxy 330 and the electronics 320 from being subjected to a prescribed temperature beyond which heat damage to the electronics 320 may occur. As before, other coupling means may also be employed.

With reference to FIGS. 10-12, a sensor unit 400 according to further embodiments of the present invention is shown therein. The sensor unit 400 includes elements 410, 420, 430 and 450 corresponding to the elements 110, 120, 130 and 150, respectively, of the sensor unit 100. The sensor unit 400 differs from the sensor unit 100 in that the plug 140 is replaced with a cap 440.

The cap 440 has an end wall 446 and a cylindrical side wall 447 together defining an interior cavity 448 and an opening 449 communicating with the cavity 448. The cavity 448 has an inner diameter K (FIG. 10) that is substantially the same as the outer diameter of the tube 410 so as to snugly overlie the same when the cap 440 is assembled to the tube 410 as shown in FIG. 11. The cavity 448 can have a depth M (FIG. 10) of between about 2 and 10 mm.

The sensor unit 400 can be assembled in substantially the same manner as the sensor unit 100 except that the cap 440 is fitted over the tube 410 and laser welded about the opening 449. The cap 440 may be formed of the same materials as discussed above with regard to the plug 140.

Figure 13:
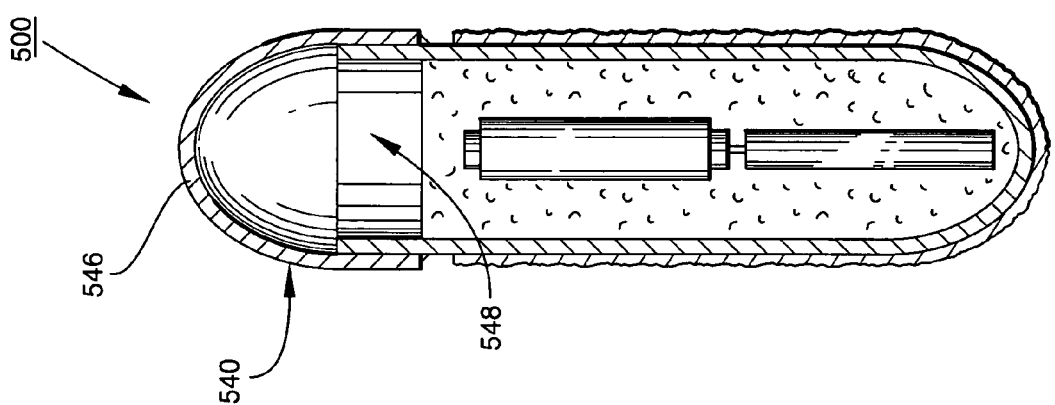
FIG. 13 is a cross-sectional view of a sensor unit according to further embodiments of the present invention.

With reference to FIG. 13, a sensor unit 500 according to further embodiments of the present invention is shown therein. The sensor unit 500 corresponds to the sensor unit 400 except that the cap 440 is replaced with a cap 540. The cap 540 corresponds to the cap 440 except that the outer end 546 of the cap 540 is dome-shaped and defines a correspondingly shaped cavity 548.

Figure 14:
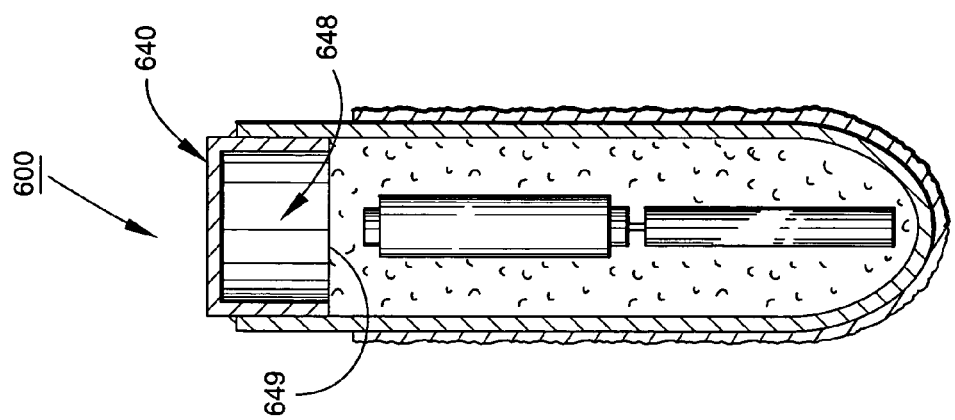
FIG. 14 is a cross-sectional view of a sensor unit according to still further embodiments of the present invention.

With reference to FIG. 14, a sensor unit 600 according to further embodiments of the present invention is shown therein. The sensor unit 600 corresponds to the sensor unit 100 except that the solid plug 140 is replaced with a hollow plug 640. The plug 640 defines a cavity 648 and a communicating inner opening 649. The plug 640 otherwise corresponds to the plug 140.

Figure 15:
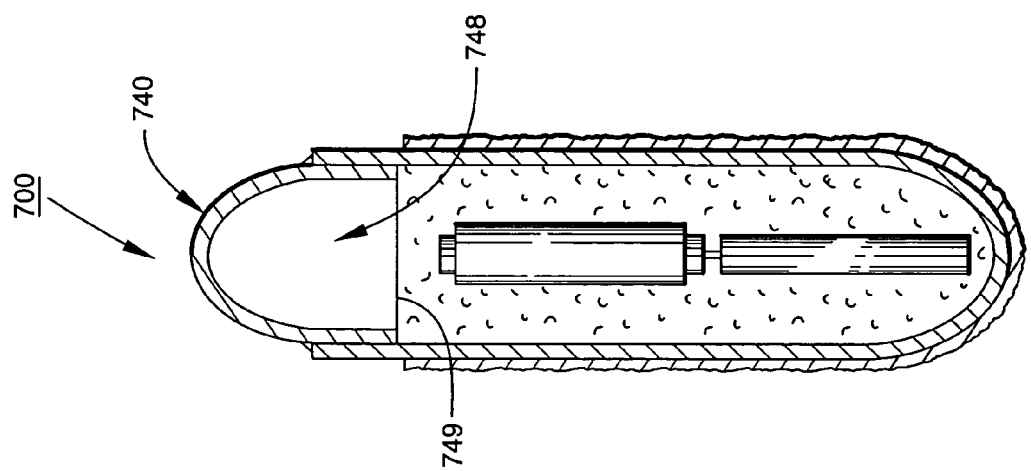
FIG. 15 is a cross-sectional view of a sensor unit according to additional embodiments of the present invention.

With reference to FIG. 15, a sensor unit 700 according to further embodiments of the present invention is shown therein. The sensor unit 700 corresponds to the sensor unit 200 (FIG. 5) except that the rounded, solid plug 240 is replaced with a rounded, hollow plug 740. The plug 740 defines a cavity 748 and a communicating inner opening 749. The plug 740 otherwise corresponds to the plug 240.

With reference to FIGS. 16-18, a sensor unit 800 according to further embodiments of the present invention is shown therein. The sensor unit 800 includes elements 810, 820, 830 and 850 corresponding to elements 110, 120, 130 and 150, respectively, except that the length of the tube 810 may be reduced as compared to the tube 110 as discussed below. The sensor unit 800 employs a retention cap 860 in place of the plug 140 (or to be attached over the plug 140).

As shown, the retention cap 860 includes a cylindrical wall 862 defining an interior passage 864. In certain embodiments, the passage 864 can extend fully between and communicates with each of an outer opening 864A and an inner opening 864B. As also shown, a shoulder 866 of enlarged diameter (as compared to the wall 862) extends about an upper portion of the wall 862. A plurality (shown as four) of fins or projections 865 extend outwardly and downwardly from the shoulder 866. The projections 865 can be equally spaced about the perimeter. Each projection 865 preferably has a length N (FIG. 17) of between about 5 and 10 mm.

The cap 860 can be formed of a polymeric material. More preferably, the cap 860 is formed of medical grade (i.e., Class VI) polypropylene or polyethylene.

The sensor unit 800 is preferably assembled in a different manner than that described above with regard to the sensor unit 100. The uncured epoxy 830 is injected into the tube 810. The electronics 820 are inserted into the uncured epoxy 830. The epoxy 830 and the electronics 820 are subjected to a vacuum atmosphere to draw out trapped air bubbles. In order to further evacuate trapped air, additional uncured epoxy 830 may be injected prior to the curing step so that the uncured epoxy overflows the tube 810. A suitable solvent may be used to clean the uncured epoxy from the outer surface of the tube 810. The retention cap 860 is inserted into the tube 810 and the epoxy 830 as shown in FIG. 17 so that a convex meniscus 832 of epoxy is formed at the opening 864A. The epoxy 830 is then allowed to cure, thereby securely bonding the retention cap 860 to the tube 810. The anti-migration coating 850 is applied to the outer surface of the tube 810, preferably after the uncured epoxy 830 is cleaned from the outer surface of the tube 810. Alternatively, the anti-migration coating 850 may be applied to the tube 810 before injecting the epoxy 830 into the tube 110.

The retention cap 860 provides a number of advantages. The projections 865 serve to mechanically engage the tissue surrounding the sensor unit 800 after the sensor unit has been injected or implanted. The passage 864 allows for a substantial engagement between the retention cap 860 and the epoxy to ensure strong retention of the cap 860 on the tube 810. Additionally, a portion 820A (e.g., a portion of the antenna coil) of the sensor electronics 820 may be received in the passage 864 so that the overall length of the sensor unit 800 may be reduced.

The procedures for removing trapped air bubbles reduce the risk of pooling of water vapor in retained air bubble voids. Such pooled water may cause corrosion of the electronics 820.

Alternatively, the retention cap 860 may be modified to include a closure wall in place of the opening 864A. More or fewer projections 865 may be provided. The projections 865 may be reversed such that the free ends thereof point away from rather than toward the end 814 (FIG. 17) of the tube 810 (i.e., upwardly rather than downwardly in the illustration of FIG. 17). The projections 865 may be adapted to expand outwardly once implanted in tissues, for example, due to exposure to heat or moisture. For example, the projections 865 may be initially held in a first position by a dissolvable bio-compatible adhesive, which adhesive dissolves once the sensor unit is implanted to allow the projections to expand. In addition, sensor units can be configured as described for other embodiments with the cap positioned over a desired region of the perimeter/outer surface of the sensor housing. Suitable modifications to the methods of forming the sensor unit 800 will be apparent to those of skill in the art.

Figure 19:
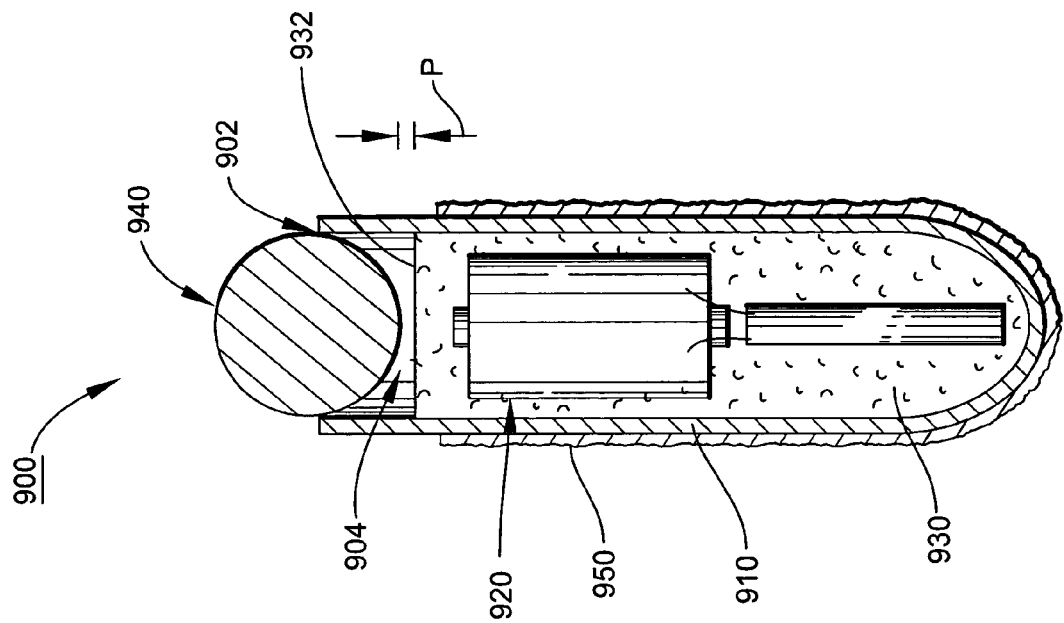
FIG. 19 is a cross-sectional view of a sensor unit according to further embodiments of the present invention.
Figure 21:
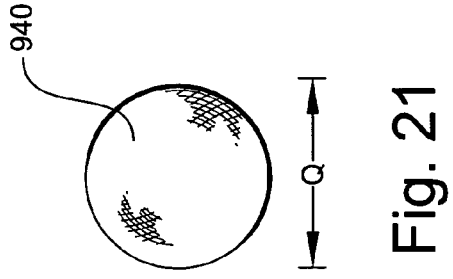
FIG. 21 is a perspective view of a spherical plug forming a part of the sensor unit of FIG. 19.
Figure 20:
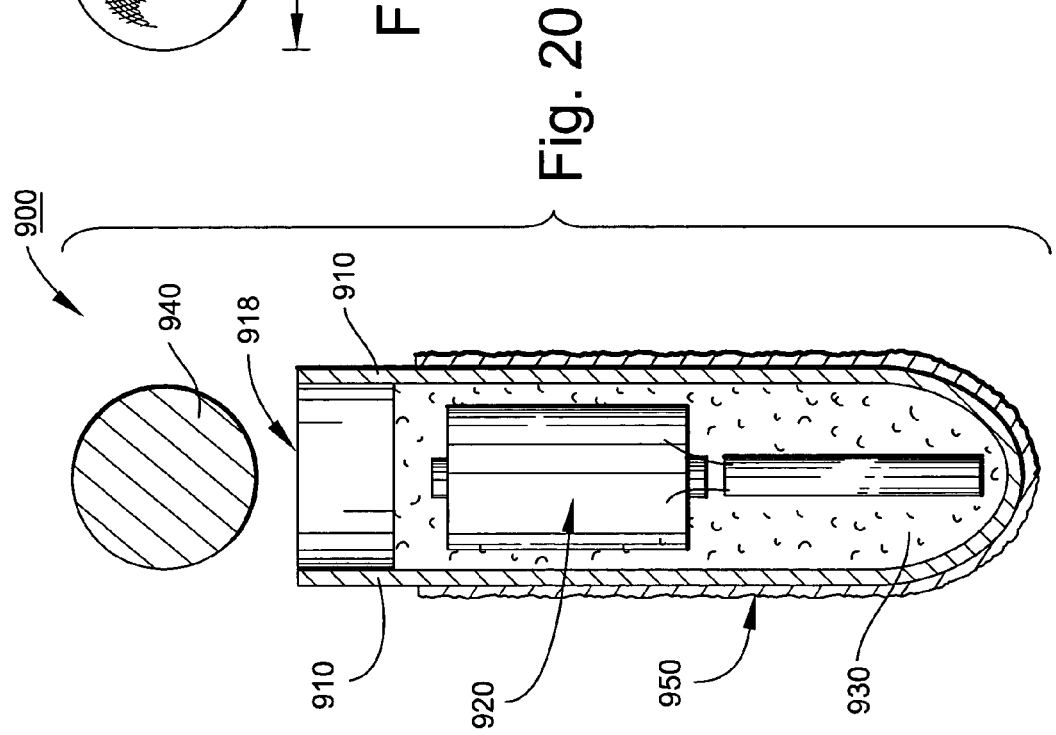
FIG. 20 is an exploded, cross-sectional view of the sensor unit of FIG. 19.

With reference to FIGS. 19-21, a sensor unit 900 according to further embodiments of the present invention is shown therein. The sensor unit 900 includes elements 910, 920, 930 and 950 corresponding to elements 110, 120, 130 and 150, respectively, of the sensor device 100. The sensor unit 900 has a plug 940 in place of the plug 140.

As best seen in FIG. 21, the plug 940 is a spherical bead. Preferably and as illustrated, the plug 940 is solid. The plug 940 has a diameter Q that is preferably the same as or slightly greater than the inner diameter of the opening 918 of the tube 910. The upper surface 932 of the epoxy 930 is positioned such that the lowermost portion of the plug 940 and the epoxy surface 932 define a gap 904 therebetween. Preferably, the gap 904 has a height P (FIG. 19) of between about 2 and 6 mm.

The plug 940 may be a laser welded or flamed in place to form a seal 902 (FIG. 19). Notably, the spherical shape of the plug 940 facilitates convenient and accurate positioning of the plug 940 the tube 910.

Figure 22:
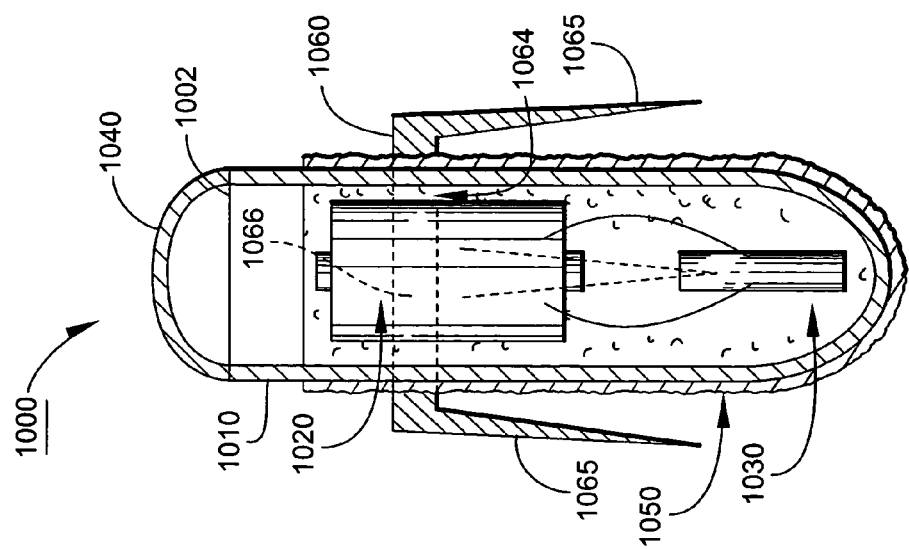
FIG. 22 is a cross-sectional view of a sensor unit according to further embodiments of the present invention.
Figure 23:
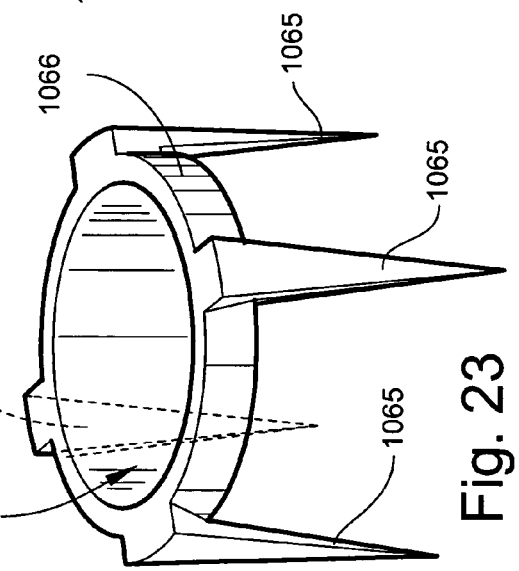
FIG. 23 is a perspective view of a retention device forming a part of the sensor unit of FIG. 22.
Figure 24:
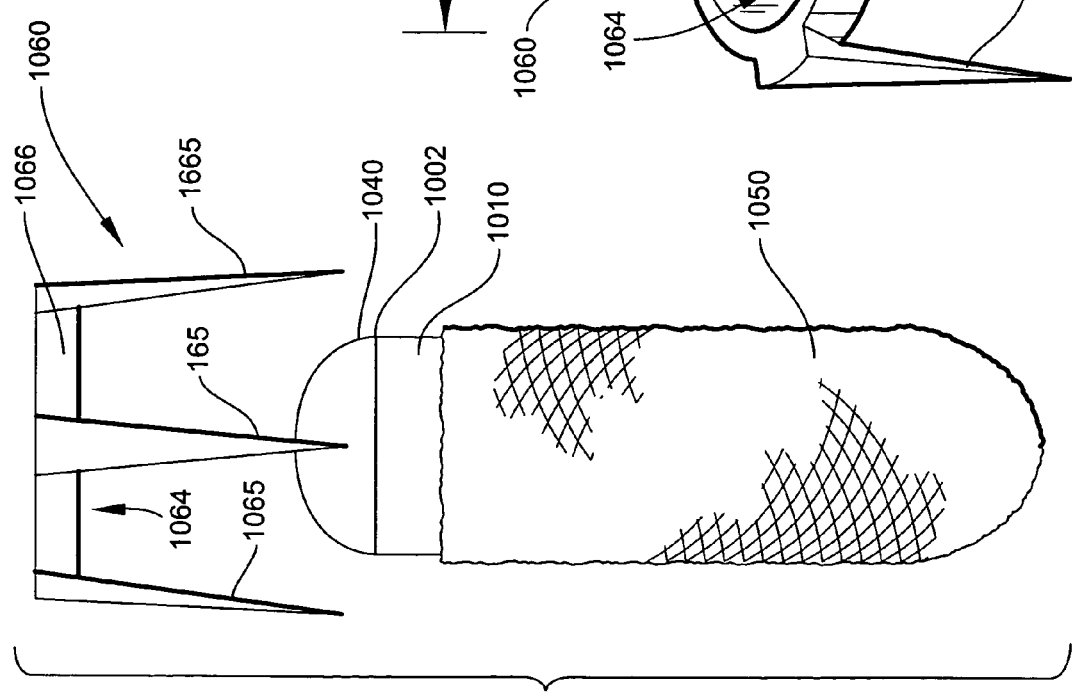
FIG. 24 is an exploded, side elevational view of the sensor unit of FIG. 22.

With reference to FIGS. 22-24, a sensor unit 1000 according to further embodiments of the invention is shown therein. The sensor unit 1000 includes elements 1010, 1020, 1030 and 1050 corresponding to elements 110, 120, 130 and 150, respectively. As illustrated in FIG. 22, a glass cap 1040 is welded (e.g., using a flame, laser or other suitable means) to the open end of the tube 1010 to form a hermetic seal. However, any of the above-described caps, plugs and methods for closing the open end of the tube may be employed.

The sensor unit 1000 also includes a retention device 1060 mounted on and surrounding a mid-portion (preferably at or near the center) of the tube 1010. The retention device 1060 may be used in place of or in addition to the retention cap 860. The retention device 1060 includes a band 1066 defining an opening 1064. Four substantially rigid projections 1065 are secured to the band 1066. In use, the projections may engage the surrounding tissue to prevent or inhibit migration in the manner discussed above with regard to the projections 865.

Preferably, the band 1066 is formed of an elastomeric material and has a relaxed diameter R (FIG. 23) that is less than the diameter of the tube 1010 at the mounting location. Suitable elastomeric materials include silicone rubber. The band 1066 is elastically stretched, slid over the tube 1010 and the coating 1050, and released so that elastic tension in the band 1066 retains the retention device 1060 on the tube 1010. Optionally or alternatively, an adhesive or the like may be used to secure the retention device 1060 in place.

Figure 25:
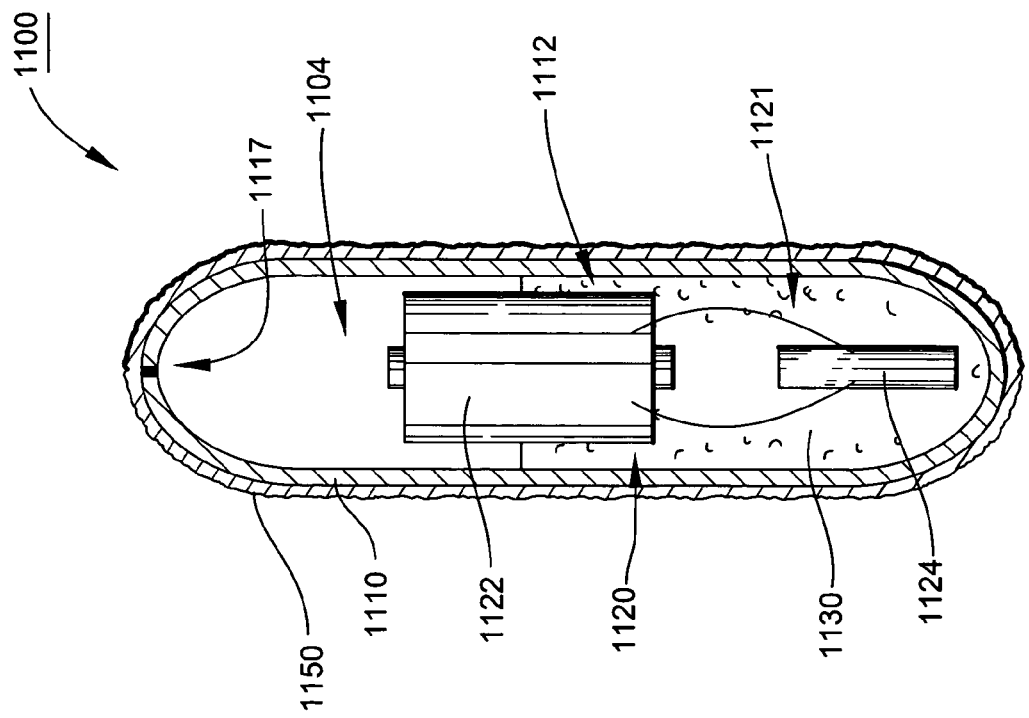
FIG. 25 is a cross-sectional view of a sensor unit according to further embodiments of the present invention.

With reference to FIG. 25, a sensor unit 1100 according to further embodiments of the invention is shown therein. The sensor unit 1100 includes a tube 1110 corresponding to the tube 110 except that, in place of the opening 118 and the plug 140, the tube 1110 has an integrally formed, hermetically sealed end portion 1117. Sensor electronics 1120 corresponding to the sensor electronics 120 are disposed in the tube chamber 1112. Epoxy potting material 1130 corresponding to the epoxy 130 is also disposed in the chamber 112 and surrounds the IC 1124, a portion or all of the antenna portion 1122 and the juncture 1121 between the portions 1124 and 1122. The cured epoxy 1130 mechanically stabilizes the portions 1124 and 1122. A remaining portion of the antenna portion 1122 is disposed in a gas-filled portion 1104 of the chamber 1112 between the epoxy 1130 and an end of the tube 1110. An anti-migration coating 1150 corresponding to the coating 150 coats (preferably, fully) the outer surface of the tube 1110.

The sensor unit 1100 may be formed in the following manner. The tube 1110 is initially open on its upper end (i.e. has a shape corresponding to that of the tube 110). A selected volume of the uncured epoxy is injected into the tube. The sensor electronics 1120 are placed into the epoxy in the tube 1110. The amount of epoxy injected into the tube is sufficient to cover the IC 1124 and at least the junction 1121. The epoxy is then cured. The open end of the tube 1110 is flame or laser welded to form the closed end portion 1117. In this manner, the tube 1110 is hermetically sealed. The anti-migration coating 1150 is applied to the outer surface of the hermetically sealed tube 1110, preferably using a VDP technique as discussed above with regard to the formation of the sensor unit 100.

Figure 26:
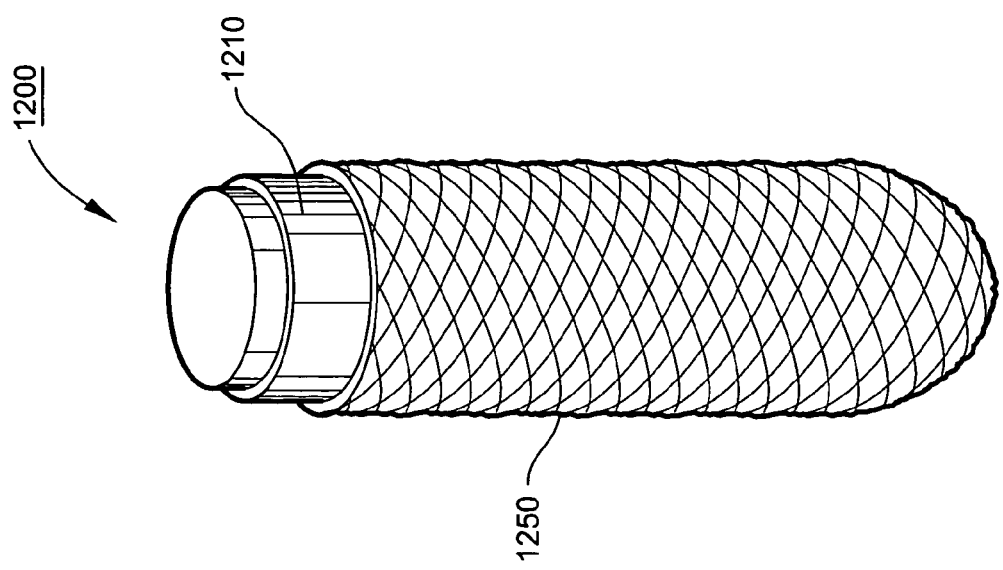
FIG. 26 is a perspective view of a sensor unit according to further embodiments of the present invention.

With reference to FIG. 26, a sensor unit 1200 according to further embodiments of the invention is shown therein. The sensor unit 1200 corresponds to the sensor unit 100 except that the anti-migration coating 150 is replaced with an anti-migration mesh layer 1250 surrounding a portion (as shown) or all of the tube 1210. The mesh layer 1250 is preferably a sleeve as shown. The mesh layer 1250 may be secured to the tube 1210 by a medical grade adhesive or by tying or fusing at one end or both ends. The mesh layer 1250 may be used in place of any of the anti-migration coatings of the above-described embodiments.

According to some embodiments, the mesh layer 1250 is formed of a non-biodegradable polymer; however, a biodegradable polymer may be used. More preferably, the mesh layer 1250 is formed of non-biodegradable polypropylene. The mesh layer may be a textile material or fabric. Alternatively, the mesh layer may be extruded and stamped with the pores, molded with the pores, or molded and then stamped. Suitable polypropylene meshes include Prolene™ polypropylene mesh available from Ethicon, Inc. The pore size of the mesh layer 1250 should be selected to allow tissue in-growth. Preferably, the pore size is greater than 25 microns.

Figure 27:
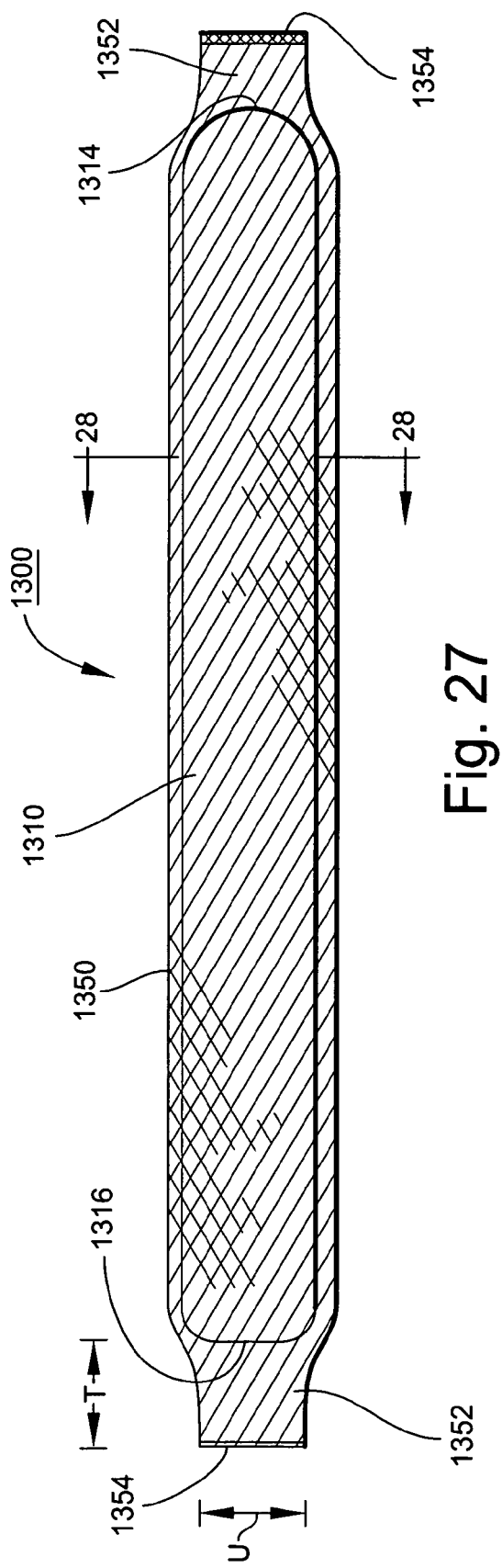
FIG. 27 is a side view of a sensor unit according to further embodiments of the present invention.
Figure 28:
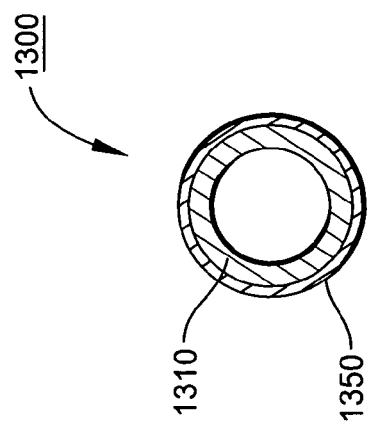
FIG. 28 is a cross-sectional view of the sensor unit of FIG. 27 taken along the line 28-28 of FIG. 27.

With reference to FIGS. 27 and 28, an implantable sensor unit 1300 according to further embodiments of the invention is shown therein. The sensor unit 1300 corresponds to the sensor unit 1100 except that the anti-migration coating 1150 is replaced with an anti-migration layer or sleeve 1350 formed of a textile material surrounding a portion or all (as shown) of the tube 1310. For clarity, only the tube 1310 (which corresponds to the tube 1110) and the anti-migration layer 1350 are shown in FIG. 28.

While a single piece housing including the tube 1310 fused closed at one end is illustrated, housings including both a tube (e.g., the tube 110) and a plug (e.g., the plug 140) may be used instead. As in the other described embodiments, the housing is preferably a hermetically sealed glass housing or capsule.

According to some embodiments, the anti-migration layer 1350 shown in FIGS. 27 and 28 is a sleeve. The sleeve may substantially conform to and fit snugly against the tube 1310. The anti-migration layer 1350 may include a pair of holding tabs 1352 extending from either end of the sensor unit 1300 and beyond the adjacent ends 1314, 1316 of the tube 1310. Alternatively, the sensor unit may have only one holding tab 1352. According to some embodiments, the anti-migration layer 1350 substantially fully envelops the housing. The ends 1354 of the sleeve-shaped anti-migration layer 1350 can be fused or otherwise closed to reliably capture and maintain the tube 1310 within the anti-migration layer 1350. Alternatively, one or both of the ends of the sleeve (and, thus, the holding tabs where provided) may be left open.

The anti-migration layer 1350 may be formed of any suitable material. According to some embodiments, the anti-migration layer 1350 is a multi-filament textile material. The anti-migration layer 1350 may be formed of a multi-filament suture material. Suitable suture materials may include, but are not limited to, silk, stainless steel, nylon, polyester, polypropylene, surgical gut, polyglactin 910, polyglycolic acid, poliglecaprone 25, polyglyconate, and polydioxanone. According to some embodiments, the anti-migration layer 1350 is a braided material. According to some embodiments, the anti-migration layer 1350 is preferably formed of polyester filaments.

According to some embodiments, the anti-migration layer 1350 is formed of filaments that are substantially non-absorbable and non-degradable in a human body. Alternatively, the anti-migration layer 1350 may be formed of filaments that are absorbable in a human body, for example, after a period of 2 to 10 weeks.

According to some embodiments, the anti-migration layer 1350 is substantially free of pores having a size greater than 15 microns. Alternatively, the anti-migration layer 1350 may be a mesh defining pores having a pore size of at least 25 microns.

The holding tabs 1352 preferably each have a length T (FIG. 27) of at least 2 mm. According to some embodiments, the length T of the holding tabs is between about 2 and 10 mm. Preferably, the thickness of each tab 1352 is between about 1 and 5 mm. Preferably, the width U of each tab 1352 is between about 50% and 100% of the outer diameter of the tube 1310. According to some embodiments, the holding tabs 1352 are preferably flexible.

Figure 29:
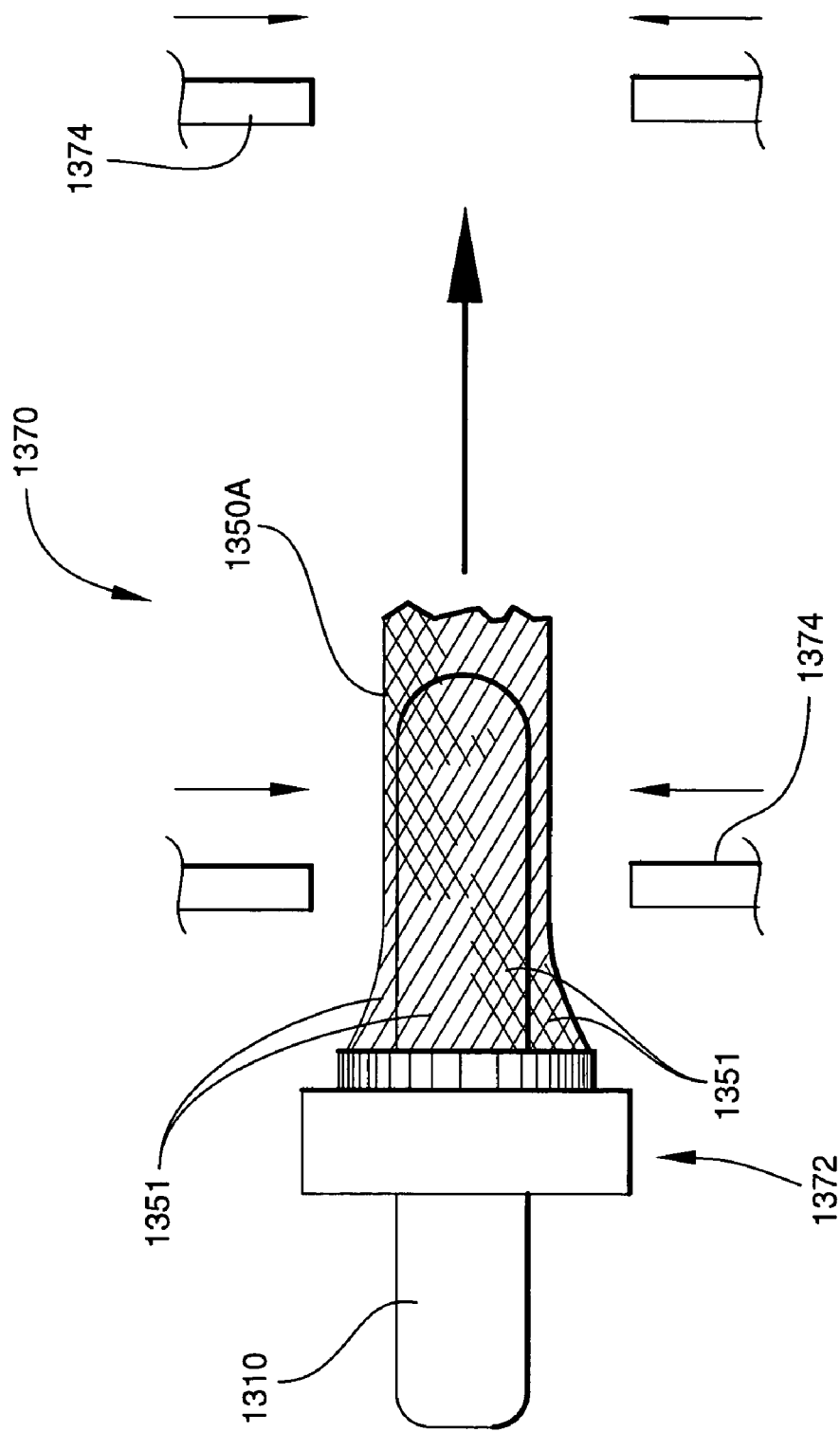
FIG. 29 is a schematic view of an apparatus for forming the sensor unit of FIG. 27.

The sensor unit 1300 may be formed by any suitable method and apparatus. According to embodiments of the present invention and with reference to FIG. 29, the sensor unit 1300 may be formed using an apparatus 1370. The apparatus 1370 includes a braiding station 1372 and a pair of spaced apart cutting/fusing stations 1374. The sealed tube 1310 with the desired electronics disposed therein, is fed through the braiding station 1372. As the tube 1310 passes through the braiding station 1372, a plurality of filaments 1351 are braided about the tube 1310 to form a continuous, braided sleeve 1350A of textile material about the tube 1310. The braiding station 1372 may include a suitably modified braiding apparatus of the type used to form braided suture material.

In operation, the sleeve 1350A can be cut and fused closed on either side of the tube 1310 by the cutting/fusing stations 1374 after or as the tube 1310 and the sleeve 1350A exit the braiding station, thereby forming the sleeve 1350 about the tube 1310. An appropriate amount of the sleeve 1350A is left on each end of the tube 1310 to form the holding tabs 1352. As an alternative or in addition to fusing the ends of the sleeve 1350 closed, the ends of the sleeve 1350 may be tied, glued or otherwise closed. A single cutting/fusing station may also be used to serially cut and fuse the opposing ends of the sleeve as the tube is fed through the apparatus.

Figure 30:
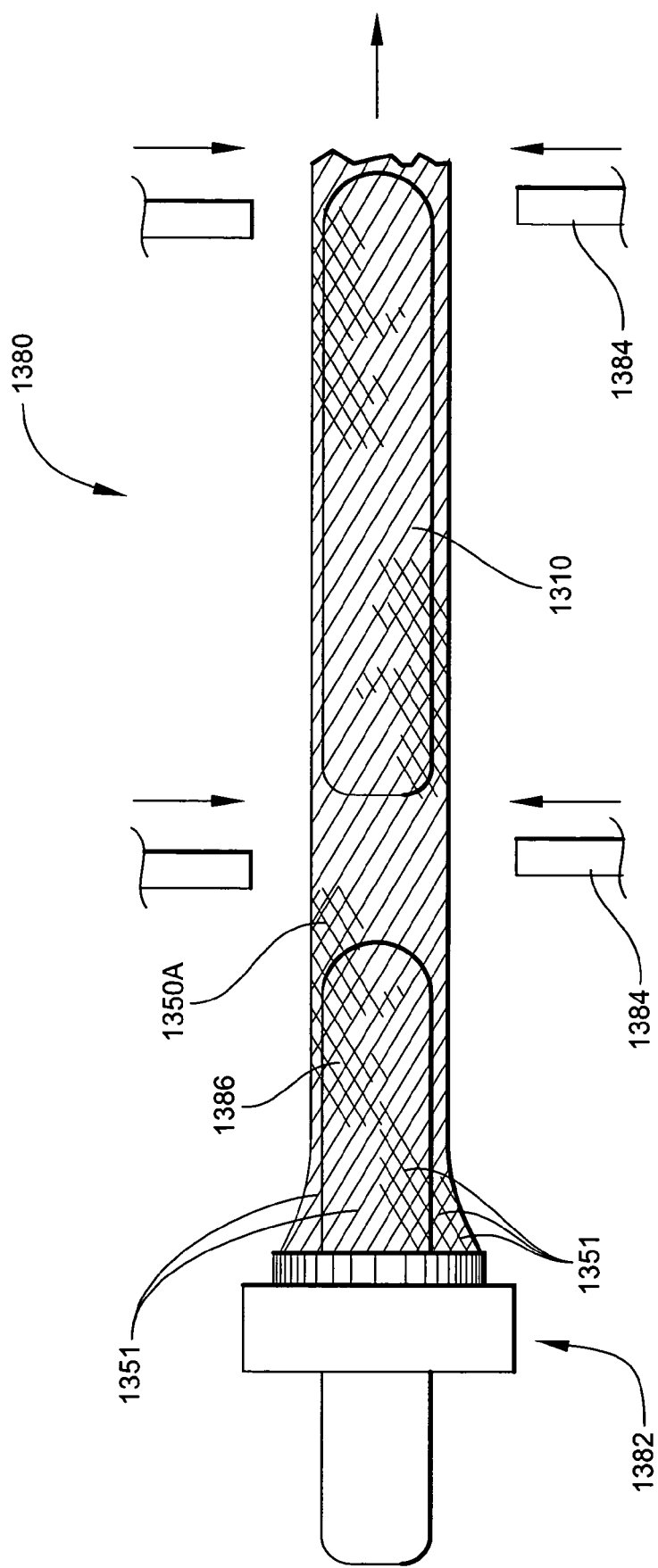
FIG. 30 is a schematic view of a further apparatus for forming the sensor unit of FIG. 27.

According to further embodiments of the present invention and with reference to FIG. 30, the sensor unit 1300 may be formed using an apparatus 1380. The apparatus 1380 has a braiding station 1382 and cutting/fusing stations 1384 and corresponds to the apparatus 1370 except for the further provision of a mandrel 1386. The braiding station 1382 forms the continuous braided sleeve 1350A of textile material on the mandrel 1386 rather than on the tube 1310. As the sleeve 1350A is generated as a continuous tubular sleeve from the braiding station, it passes downstream over the tube 1310. The sleeve 1350A is then cut and fused closed on either side of the tube 1310 by the cutting/fusing stations 1384 in the same manner as discussed above.

According to alternative method embodiments, the sleeve 1350A may be cut to length and then pulled over the tube 1310, rather than sliding the sleeve onto the tube 1310 from the mandrel 1386 before cutting.

Figure 31:
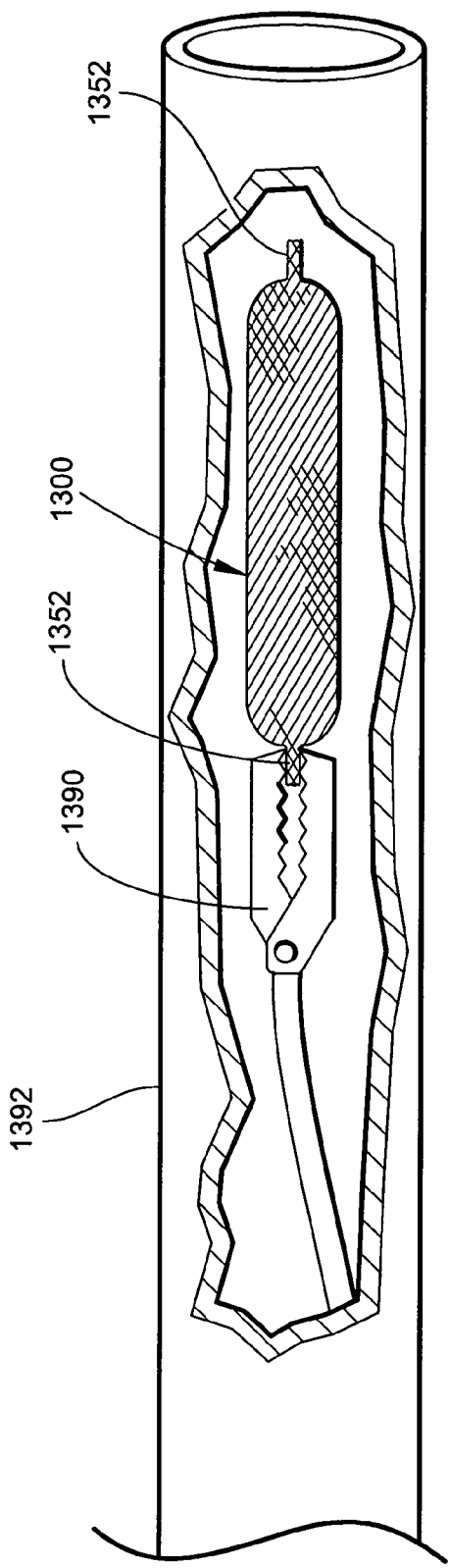
FIG. 31 is a partial, fragmentary, enlarged perspective view of the sensor unit of FIG. 27 being held by an instrument in a canula.

The holding tabs 1352 may be used to facilitate handling of the sensor unit 1300. The holding tabs 1352 may be grasped, hooked, adhered to or otherwise held to allow transport, positioning and/or repositioning of the sensor unit. It is particularly contemplated that the holding tabs 1352 may be used to handle the sensor unit 1300 while performing surgical procedures (i.e., intraoperatively). The holding tabs may be used to position the sensor unit 1300 in the body during open surgery or using an instrument or insertion tool 1390 (e.g., an endoscope) through a canula 1392 as shown in FIG. 31. The holding tabs 1352 may be used to hold and manipulate the sensor unit 1300 during laparoscopic surgery or similar surgeries using hollow canulas, for example.

Figure 32:
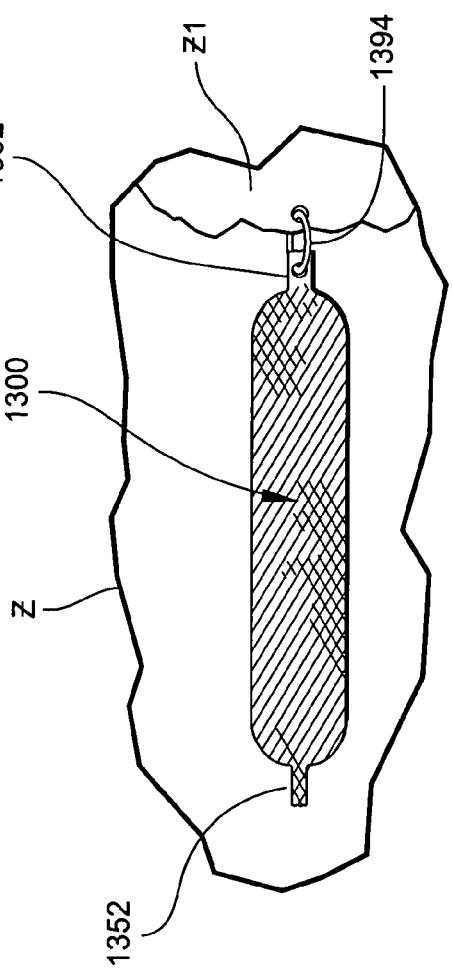
FIG. 32 is a partial, fragmentary, schematic view of the sensor unit of FIG. 27 implanted in a body and secured to tissue of the body by a suture.

The holding tabs 1352 may also be used to secure the sensor unit 1300 to a desired substrate temporarily or indefinitely. For example, the sensor unit 1300 may be secured to the substrate (such as tissue) using one or more sutures, staples or the like extending through the holding tab or tabs 1352. FIG. 32 shows the sensor unit 1300 implanted in a body Z and secured to tissue Z1 of the body Z by a suture 1394 that extends through the holding tab 1352 and the tissue Z1.

One or both of the holding tabs 1352 may be omitted. The holding tabs 1352 may be formed of a material other than a textile material. The holding tabs may be otherwise secured to the sensor housing. For example, the holding tabs may be fastened or adhered to the sensor housing, or may be integrally formed with or embedded in the sensor housing. The sensor units 100-1200 described above may be modified to include one or more holding tabs as described herein.

Figure 33:
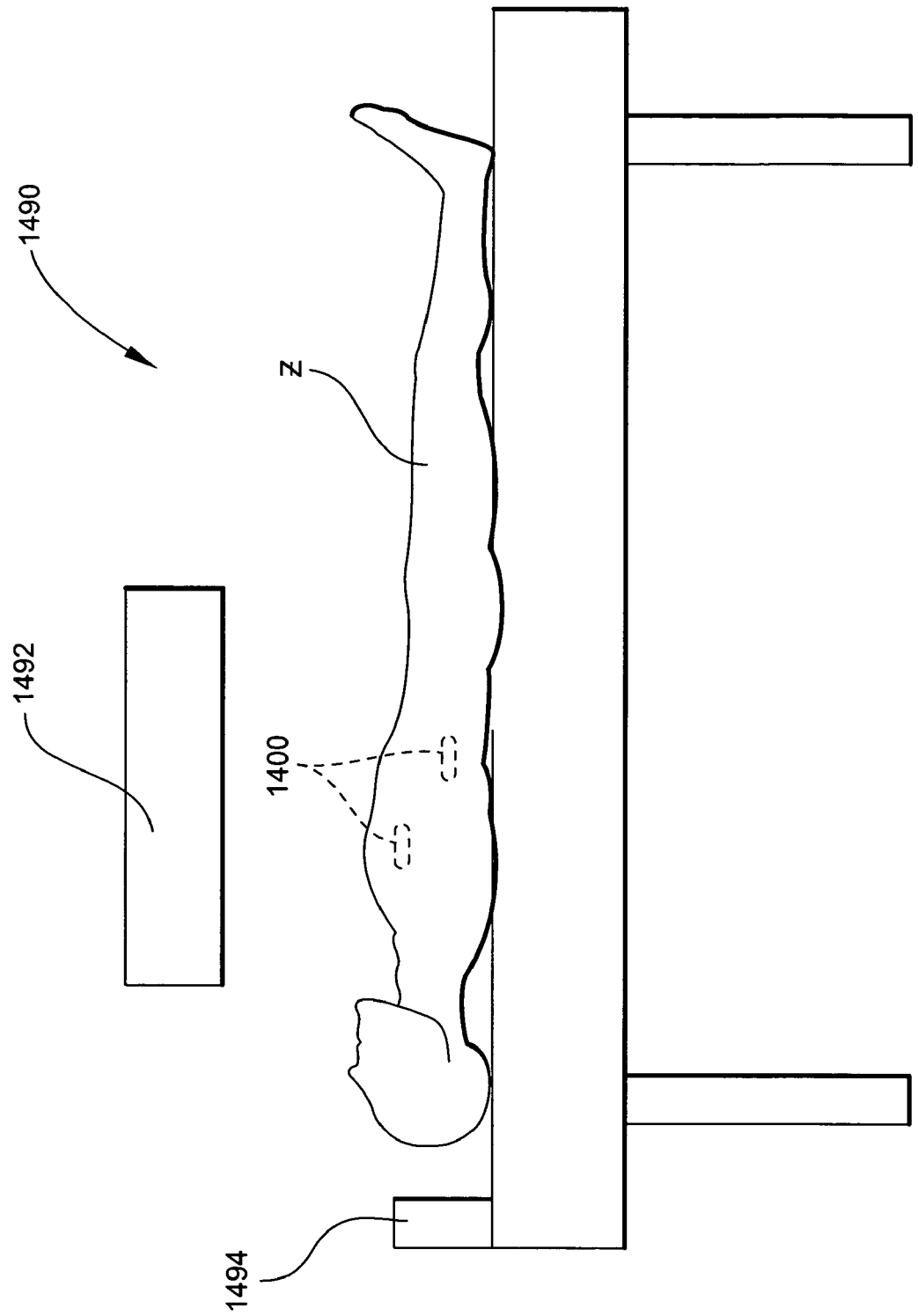
FIG. 33 is a schematic view of an imaging system employing a sensor unit according to embodiments of the present invention.
Figure 34:
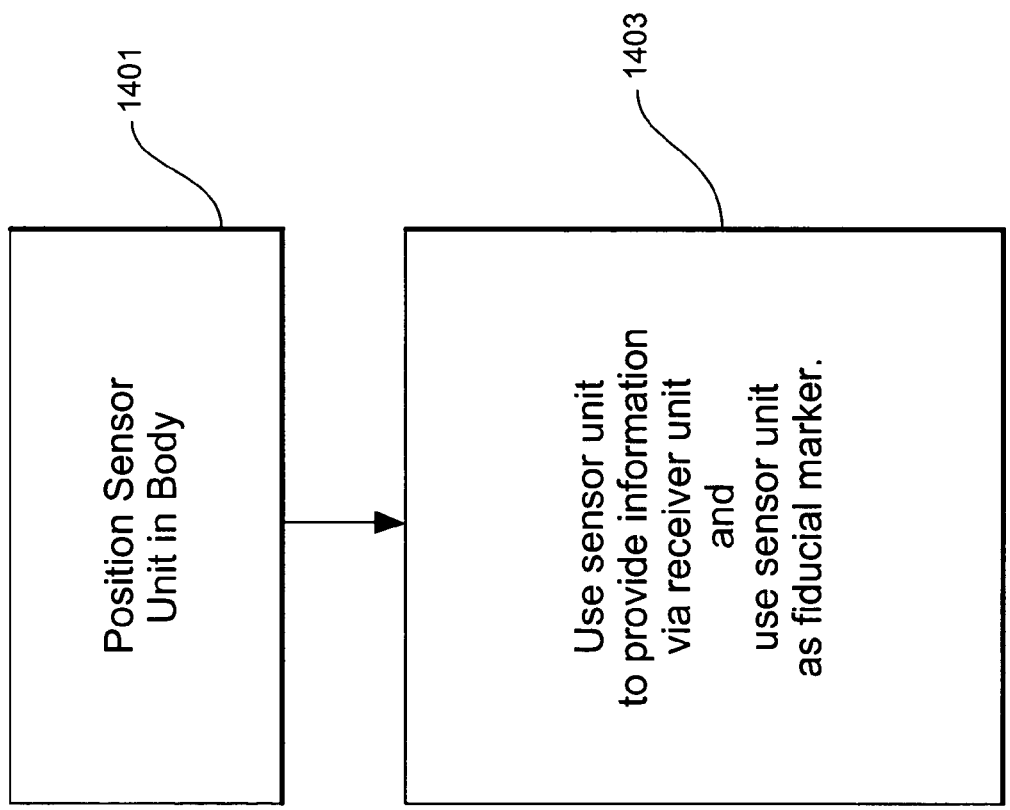
FIG. 34 is a flow chart representing operations for using an implantable sensor unit in an imaging procedure according to embodiments of the present invention.

With reference to FIGS. 33 and 34, in accordance with method embodiments of the present invention, an implantable sensor unit 1400 is used in an imaging system 1490 to facilitate an imaging procedure such as a radiographic scan. Non-X-ray imaging procedures may also be used such as ultrasound or MRI. The implanted sensor unit 1400 is capable of emitting a signal (e.g., wirelessly or via wiring) for communication with a receiver unit 1494 located outside of a body Z. At least a portion of the sensor unit 1400 can be formed of a material that is highly detectable to a sensing apparatus 1492, such a planar film (X-ray) machine, a computer tomography machine or other radiographic sensing apparatus. For example, the sensor unit 1400 may include a sufficient amount of a radiopaque material to be imaged during normal imaging procedures. Suitable radiopaque materials may include ferrite material or radiopaque epoxies, coatings, inks, thin-films, paints, tapes, strips, and the like. The sensor unit 1400 may be an implantable sensor unit as described above in accordance with various embodiments of the present invention.

The sensor unit 1400 can be inserted and positioned in the body Z by any suitable means (Block 1401; FIG. 34). The body Z is then scanned, for example, in conventional manner, using the sensing apparatus 1492 (Block 1403). The sensor unit 1400 is highly visible on the scan results, thereby serving as a fiducial marker. For example, where the sensor unit 1400 is radiopaque and the sensing apparatus 1492 is a radiographic sensing apparatus, the sensor unit 1400 blocks the transmission of X-rays to provide a contrasting image. The opacity, degree of contrast, and sharpness of the image may vary with the material and type of process used to create the sensor unit 1400. Additionally, the sensor unit 1400 serves to provide information as discussed above via communication with the receiver unit 1494 (Block 1403). One or more additional sensor units 1400 may be implanted and used as fiducial markers and/or information providers.

Figure 35:
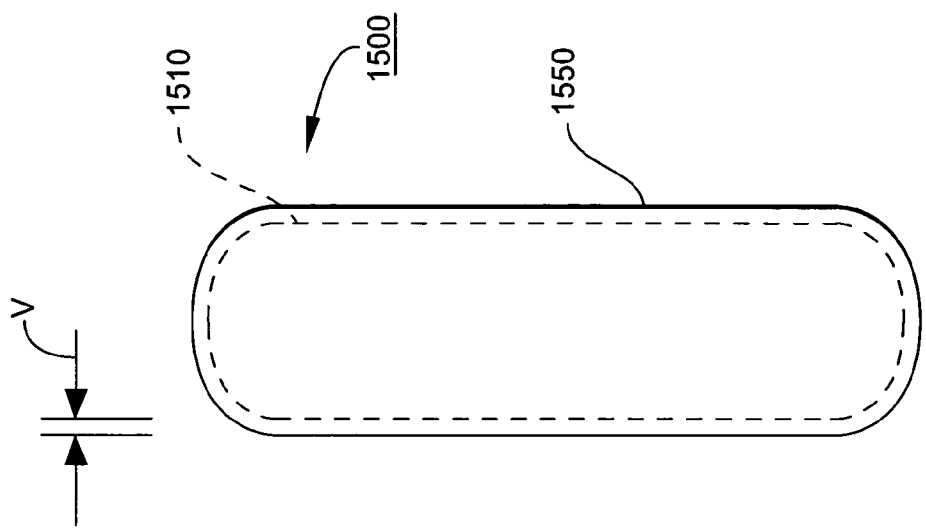
FIG. 35 is a side view of a sensor unit according to further embodiments of the present invention.

With reference to FIG. 35, an implantable sensor unit 1500 according to further embodiments of the present invention is shown therein. The sensor unit 1500 corresponds to the sensor unit 1100 except that the anti-migration coating 1150 is replaced with a bio-compatible anti-migration layer or tube 1550 formed of a heat shrinkable thermoplastic material surrounding a portion or all (as shown) of the tube 1510 (which corresponds to the tube 1110).

The layer 1550 is preferably formed of a heat shrinkable thermoplastic resin. According to some embodiments, the layer 1550 preferably has a thickness V of between about 1 and 3 mm. The layer 1550 may be free of apertures or may have one or more holes punched or otherwise formed therein.

The layer 1550 may be installed on the tube 1510 in the following manner. A tube of the heat shrinkable material is placed about the sealed tube 1510. The tube of heat shrinkable material is then heated, using a suitable heating device, to a temperature sufficient to shrink the material. The tube of heat shrinkable material contracts to fit snugly and securely about the tube 1510, thereby forming the anti-migration layer 1550.

If desired, one or both of the ends of the tube of heat shrinkable material may be closed (e.g., by fusing) or left open. The layer 1550 may be formed so as to include one or more holding tabs corresponding to the holding tabs 1352.

Following formation, each of the above-described sensor units is preferably subjected to a leak test to confirm that a proper hermetic seal has been achieved. The sensor units may be evaluated using a helium mass spectrometer leak detection test. Those sensor units which have leak rates exceeding a selected maximum leak rate may be discarded. Preferably, the hermetic seal provided by each hermetically sealed sensor unit is such that under a helium mass spectrometer leak detection test in accordance with Military Standard 202F, Test Condition C, the measured leak rate is less than about $1 \times 10^{-8}$ atm-cc/s.

Each of the sensor units according to the present invention preferably has an overall length of no more than 27 mm and an overall maximum outer diameter of no more than 3.5 mm.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for obtaining data using an implantable sensor unit in a body of a patient, the method comprising:
   a) implanting the sensor unit in the body at a position adjacent or in a cancerous tumor;
   b) conducting an imaging procedure on the body, including using the sensor unit in the body as a fiducial marker;
   c) detecting externally generated radiation using the sensor unit in the body; and
   d) transmitting data used to measure the detected externally generated radiation from the sensor unit to a remote receiver unit.

2. The method of claim 1 wherein the imaging procedure includes a radiographic imaging procedure and wherein at least a portion of the sensor unit is radiopaque.

3. The method of claim 1 further including:
   implanting at least one additional sensor unit in the body; and
   using the at least one additional sensor unit as a fiducial marker or fiducial markers for the imaging procedure.

4. The method of claim 3 further including:
   implanting a plurality of additional sensor units in the body; and
   using each of the plurality of additional sensor units as fiducial markers for the imaging procedure.

5. The method of claim 1 further including:
   implanting at least one additional sensor unit in the body;
   detecting an additional parameter using the at least one additional sensor unit in the body; and
   transmitting data associated with the detected additional parameter from the at least one additional sensor unit to the remote receiver unit.

6. The method of claim 1 wherein the sensor unit includes a sensor housing comprising glass.

7. The method of claim 1 wherein the sensor unit includes a sensor housing defining a chamber and includes sensor electronics disposed in the chamber, wherein the sensor electronics are adapted to wirelessly transmit data.

8. The method of claim 7 wherein the sensor unit further includes:
   an epoxy disposed in a first portion of the chamber and encapsulating at least a portion of the sensor electronics; and
   a gas disposed in a second portion of the chamber between the epoxy and an end portion of the sensor housing.

9. The method of claim 7 wherein the sensor unit is configured to wirelessly transmit data from an in vivo position to the remote receiver over a period of at least about four weeks and wherein the sensor housing is adapted to provide a hermetic seal about the sensor electronics for a period of at least about four weeks, wherein the hermetic seal is such that under a helium mass spectrometer leak detection test, the sensor housing has a leak rate that is less than about $10^{-8}$ atm-cc/s.

10. The method of claim 7 wherein the sensor electronics include a first portion and a second portion joined to the first portion at a junction, the sensor unit further includes an epoxy disposed in the chamber and surrounding the junction, and the epoxy mechanically stabilizes the first and second portions.

11. The method of claim 1 wherein the sensor unit includes a sensor housing having a length of no more than about 27 mm and an outer diameter of no more than about 3.5 mm.

12. The method of claim 1 wherein the sensor unit includes a sensor housing that is hermetically sealed.

13. The method of claim 1 wherein the sensor unit includes a sensor housing that is laser welded.

14. The method of claim 1 wherein the sensor unit includes a sensor housing that is flame sealed.

15. The method of claim 1 wherein the sensor unit includes a sensor housing having an outer surface, the sensor unit further includes a bio-compatible anti-migration layer encasing at least a portion of the outer surface of the sensor housing, and the anti-migration layer is formed of a textile material.

16. The method of claim 15 wherein the anti-migration layer is a flexible sleeve.

17. The method of claim 16 wherein the sleeve fully envelops the sensor housing.

18. The method of claim 15 wherein the anti-migration layer comprises a multi-filament textile material.

19. The method of claim 18 wherein the anti-migration layer comprises a multi-filament suture material.

20. The method of claim 18 wherein the anti-migration layer comprises a braided material in which one or more strands half twist alternately about two or more adjacent strands.

21. The method of claim 18 wherein the anti-migration layer comprises polyester filaments.

22. The method of claim 15 wherein the textile material includes a polyester mesh.

23. The method of claim 15 wherein the textile material is substantially non-absorbable and non-degradable in a human body.

24. The method of claim 15 wherein the anti-migration layer includes a sleeve of the textile material, wherein an end of the sleeve is closed to form a holding tab, the holding tab being adapted to facilitate handling of the sensor housing.

25. The method of claim 1 wherein the sensor unit includes a sensor housing and a holding tab extending beyond an end of the sensor housing, the holding tab being adapted to facilitate handling of the sensor housing.

26. The method of claim 25 wherein the holding tab is flexible.

27. The method of claim 25 including affixing the sensor unit to local tissue of the body using the holding tab.

28. The method of claim 27 including affixing the sensor unit to local tissue of the body using at least one suture or staple extending through the holding tab and the tissue.

29. The method of claim 1 wherein the sensor unit further includes a sensor housing and a retention device mounted on the sensor housing, the retention device including at least one projection extending away from the sensor housing.

30. The method of claim 29 wherein the retention device includes a band surrounding a portion of the sensor housing.

31. The method of claim 1 wherein the sensor unit includes means to retain the sensor unit in an implanted position in the body during at least the steps of conducting the imaging procedure and detecting the parameter.

32. The method of claim 1 wherein each of the sensor units includes a respective sensor housing and the sensor units are spaced apart from one another in the body.

33. The method of claim 32 further including:
detecting an additional parameter using the at least one additional sensor unit in the body; and
transmitting data associated with the detected additional parameter from the at least one additional sensor unit to the remote receiver unit.

34. A method for obtaining data using a plurality of implantable sensor units in a body of a patient, the method comprising:
implanting a first sensor unit in the body at a first position adjacent or in a cancerous tumor, the first sensor unit having a first sensor housing;
implanting a second sensor unit in the body at a second position spaced apart from the first sensor unit, the second sensor unit having a second sensor housing;
conducting an imaging procedure on the body, including using the first and second sensor units in the body as fiducial markers;
detecting a parameter using at least one of the first and second sensor units in the body; and
transmitting data associated with the parameter from the at least one of the first and second sensor units to a remote receiver unit.

35. The method of claim 34 including:
detecting a first parameter using the first sensor unit in the body; and
transmitting data associated with the first parameter from the first sensor unit to the remote receiver unit;
detecting a second parameter using the second sensor unit in the body; and
transmitting data associated with the second parameter from the second sensor unit to the remote receiver unit.

* * * * *